US009450191B2

(12) United States Patent
Zambianchi et al.

(10) Patent No.: US 9,450,191 B2
(45) Date of Patent: *Sep. 20, 2016

(54) THIENO[2,3-C]PYRROLE-DIONE DERIVATIVES AND THEIR USE FOR ORGANIC SEMICONDUCTORS

(71) Applicant: E.T.C. S.R.L., Bologna (BO) (IT)

(72) Inventors: Massimo Zambianchi, Cesena (IT); Laura Favaretto, Ozzano nell'Emilia (IT); Manuela Melucci, Bologna (IT); Michele Muccini, Bologna (IT); Raffaella Capelli, Bologna (IT)

(73) Assignee: E.T.C. S.R.L., Bologna (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/436,856

(22) PCT Filed: Nov. 15, 2013

(86) PCT No.: PCT/IB2013/060162
§ 371 (c)(1),
(2) Date: Apr. 17, 2015

(87) PCT Pub. No.: WO2014/076662
PCT Pub. Date: May 22, 2014

(65) Prior Publication Data
US 2015/0287932 A1    Oct. 8, 2015

(30) Foreign Application Priority Data

Nov. 16, 2012 (IT) .............................. MI2012A1952

(51) Int. Cl.
| C07D 495/04 | (2006.01) |
| C09K 11/06 | (2006.01) |
| H01L 51/00 | (2006.01) |
| H01L 51/05 | (2006.01) |
| H01L 51/52 | (2006.01) |

(52) U.S. Cl.
CPC ......... *H01L 51/0071* (2013.01); *C07D 495/04* (2013.01); *C09K 11/06* (2013.01); *H01L 51/00* (2013.01); *H01L 51/0036* (2013.01); *H01L 51/0068* (2013.01); *H01L 51/0074* (2013.01); *C09K 2211/1007* (2013.01); *C09K 2211/1014* (2013.01); *C09K 2211/1029* (2013.01); *C09K 2211/1051* (2013.01); *C09K 2211/1092* (2013.01); *H01L 51/0545* (2013.01); *H01L 51/0558* (2013.01); *H01L 51/5296* (2013.01)

(58) Field of Classification Search
CPC ... C07D 495/04; C09K 11/06; H01L 51/007; H01L 51/0068; H01L 51/0074
USPC ............................ 548/453, 126, 466; 257/40
See application file for complete search history.

(56) References Cited

U.S. PATENT DOCUMENTS

| 5,276,009 A | 1/1994 | Muenster et al. | |
| 2015/0214488 A1* | 7/2015 | Melucci ............... | H01L 51/0068 257/40 |
| 2015/0236270 A1* | 8/2015 | Melucci ............... | H01L 51/0071 257/40 |
| 2015/0311448 A1* | 10/2015 | Melucci ............... | C07D 495/04 257/40 |

FOREIGN PATENT DOCUMENTS

| DE | 1954550 A1 | 7/1971 |
| EP | 0467206 A2 | 1/1992 |
| FR | 2066727 A5 | 8/1971 |
| JP | 2009/099942 | 5/2009 |
| WO | 2006/094292 A2 | 9/2006 |
| WO | 2008/127029 | 10/2008 |
| WO | 2010/131764 | 11/2010 |

OTHER PUBLICATIONS

International Search Report issued on Jan. 29, 2014 for PCT/IB2013/060162 which was filed on Nov. 15, 2013 in the name of E.T.C. S.R.L.
Written Opinion issued on Jan. 29, 2014 for PCT/IB2013/060162 which was filed on Nov. 15, 2013 in the name of E.T.C. S.R.L.
Bijleveld, J. et al. "Poly(diketopyrrolopyrrole-terthiophene) for Ambipolar Logic and Photovoltaics" J. Am. Chem, Soc. 2009, vol. 131, pp. 16616-16617.
Facchetti, A. et al. "Building Blocks for n-Type Organic Electronics: Regiochemically Modulated Inversion of Majority Carrier Sign in Perfluoroarene-Modified Polythiophene Semiconductors" Angew. Chem. Int. Ed. 2003, vol. 42, pp. 3900-3903.
Gaina, C. et al. "Polyimides containing 1,4-dithiine units and their corresponding thiophene 2,3,4,5 tetracarboxylimide units" High Perform, Polym. 1999, vol. 11, pp. 185-195.
Letizia, J. et al. "n-Channel Polymers by Design: Optimizing the Interplay of Solubilizing Substituents, Crystal Packing, and Field-Effect Transistor Characteristics in Polymeric Bithiophene-Imide Semiconductors" J. Am. Chem. Soc. 2008, vol. 130, pp. 9679-9694.
Melucci, M. et al. "Thienopyrrolyl dione end-capped oligothiophene ambipolar semiconductors for thin film- and light emitting transistors" Chem. Commun. 2011, vol. 47, pp. 11840-11842.
Muccini, M. "A bright future for organic field-effect transistors" Nature Materials, Aug. 2006, vol. 5, pp. 605-613.
Nielsen, C. et al. "New Regiosymmetrical Dioxopyrrolo- and Dihydropyrrol- Functionalized Polythiophenes" Organic Letters, 2004, vol. 6, No. 19, pp. 3381-3384.
Pomerantz, M. "Planar 2,2'-bithiophenes with 3,3'- and 3,3',4,4'-substituents. A computational study" Tetrahedron Letters, 2003, vol. 44, pp. 1563-1565.
Ronova, I. et al. "The Effect of the Conformational Rigidity on the Initial Decomposition Temperature of some Heterocyclic Polyimides" High Performance Polymers, 2002, vol. 14, pp. 195-208.

(Continued)

Primary Examiner — Alicia L Otton
Assistant Examiner — Sagar Patel
(74) Attorney, Agent, or Firm — Steinfl & Bruno, LLP

(57) ABSTRACT

Compounds of formulae (I) and (II) useful as organic semiconductor materials, and semiconductor devices containing such organic semiconductor materials are described.

15 Claims, 6 Drawing Sheets

(56) References Cited

OTHER PUBLICATIONS

Sonar, P. et al. "A Low-Bandgap Diketopyrrolopyrrole-Benzothiadiazole-Based Copolymer for High-Mobility Ambipolar Organic Thin-Film Transistors" Adv. Mater. 2010, vol. 22, pp. 5409-5413.
Hong, W. et al. "Linear Fused Dithieno[2,3-b:3'2'-d]-thiophene Diimides" Organic Letters, 2011, vol. 13, No. 6, pp. 1410-1413.
Yoon, M-H. et al. "Organic Thin-Film Transistors Based on Carbonyl-Functionalized Quaterthiophenes: High Mobility N-Channel Semiconductors and Ambipolar Transport" J. Am. Chem. Soc. 2005, vol. 127, pp. 1348-1349.
Zhang, Q. et al. "Alternating Donor/Acceptor Repeat Units in Polythiophenes. Intramolecular Charge Transfer for Reducing Band Gaps in Fully Substituted Conjugated Polymers" J. Am. Chem Soc. Jun. 10, 1998, vol. 120, No. 22, pp. 5355-5362.
International Search Report for PCT/IB2013/059200 filed Oct. 8, 2013 on behalf of E.T.C. S.R.L. Mail Date: Dec. 13, 2013. 3 pages.
Written Opinion for PCT/IB2013/059200 filed Oct. 8, 2013 on behalf of E.T.C. S.R.L. Mail Date: Dec. 13, 2013. 4 pages.
International Search Report for PCT/IB2013/060128 filed Nov. 14, 2013 on behalf of E.T.C. S.R.L. Mail Date: Jan. 7, 2014. 4 pages.
International Search Report for PCT/IB2013/060128 filed Nov. 14, 2013 on behalf of E.T.C. S.R.L. Mail Date: Jan. 7, 2014. 6 pages.
International Search Report of the International Preliminary Examining Authority for PCT/IB2013/060128 filed Nov. 14, 2013 on behalf of E.T.C. S.R.L. Mail Date: Nov. 3, 2014. 6 pages.
International Preliminary Report on Patentability for PCT/IB2013/060128 filed Nov. 14, 2013 on behalf of E.T.C. S.R.L. Mail Date: Jan. 23, 2015. 21 pages.
Restriction Requirement for U.S. Appl. No. 14/423,074, filed Feb. 20, 2015 on behalf of Manuela Melucci. Mail Date: Apr. 22, 2016. 9 pages.
Non-Final Office Action for U.S. Appl. No. 14/435,411, filed Apr. 13, 2015 on behalf of Manuela Melucci. Mail Date: Jan. 13, 2016. 34 pages.
International Search Report for PCT/IB2012/052503 filed May 18, 2012 on behalf of E.T.C. S.R.L. Mail Date: Jul. 5, 2012. 4 pages.
Written Opinion for PCT/IB2012/052503 filed May 18, 2012 on behalf of E.T.C. S.R.L. Mail Date: Jul. 5, 2012. 6 pages.
International Preliminary Report on Patentability for PCT/IB2012/052503 filed May 18, 2012 on behalf of E.T.C. S.R.L. Mail Date: May 24, 2013. 22 pages.
Non-Final Office Action for U.S. Appl. No. 14/114,892, filed Mar. 25, 2014 on behalf of Manuela Melucci. Mail Date: Jun. 17, 2014. 13 pages.
Non-Final Office Action for U.S. Appl. No. 14/570,777, filed Dec. 15, 2014 on behalf of Manuela Melucci. Mail Date: Aug. 10, 2015. 12 pages.
Final Office Action for U.S. Appl. No. 14/570,777, filed Dec. 15, 2014 on behalf of Manuela Melucci. Mail Date: Jan. 29, 2016. 11 pages.

* cited by examiner

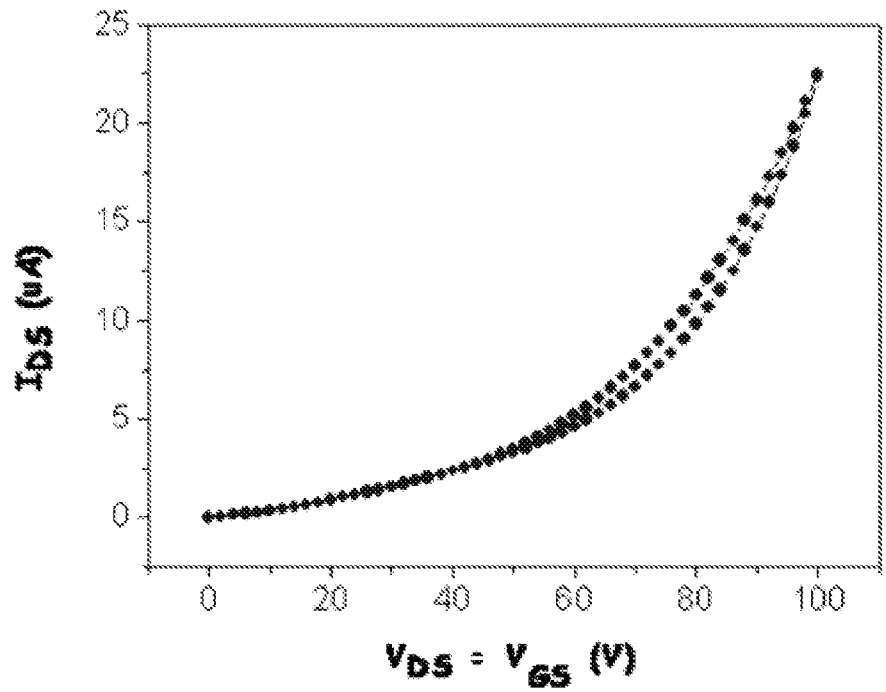
a)
Fig.3
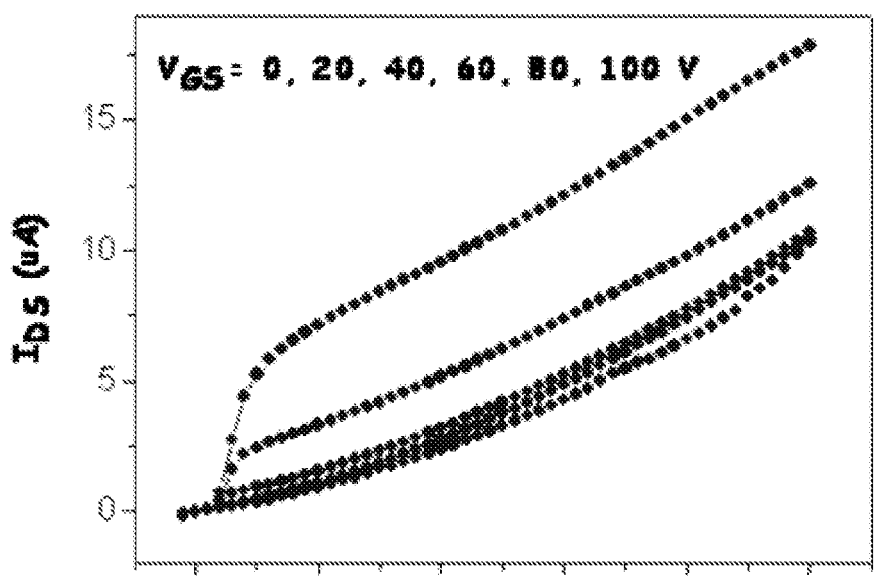

THIENO[2,3-C]PYRROLE-DIONE DERIVATIVES AND THEIR USE FOR ORGANIC SEMICONDUCTORS

CROSS REFERENCE TO RELATED APPLICATIONS

The present application is the US national stage of International Patent Application PCT/IB2013/060162 filed internationally on Nov. 15, 2013 which, in turn, claims priority to Italian Patent Application No. MI2012A001952 filed on Nov. 16, 2012.

The present invention relates to a novel n-type organic semiconductor material, and semiconductor devices containing said n-type organic semiconductor material.

It is known that organic semiconductors are materials into which charge can be reversibly introduced by the application of electromagnetic energy or chemical dopants. The electronic conductivity of these materials lies between that of metals and insulators, spanning a broad range of $10^{-9}$ to $10^3$ $\Omega^{-1}$ $cm^{-1}$. As in traditional inorganic semiconductors, organic materials can function either as p-type or n-type. In p-type semiconductors the majority carriers are holes, while in n-type the majority carriers are electrons.

The vast majority of the prior art has focused on the design, synthesis, and structure-property relationships of p-type organic semiconductor materials, including: oligoacenes, fused oligothiophenes, anthradithiophenes, carbazoles, oligophenylenes, and oligofluorenes, some of which have resulted in field-effect transistors with performance superior to amorphous silicon. In contrast, the development of n-type oligomer and polymer semiconductors has lagged behind p-type materials. In fact, compared to the p-type semiconductors, n-type semiconductors are still not fully developed, and the performances are not satisfactory.

Organic semiconductors that possess a high electron affinity are however also required, as both p- and n-channel materials are required for efficient logic circuits and organic solar cells. Indeed, n-type organic field-effect transistors are envisioned as key components of organic p-n junctions, bipolar transistors, and complementary integrated circuits leading to flexible, large-area, and low-cost electronic applications.

A variety of organic semiconductors have been considered in the art as n-type organic semiconductor materials.

Aromatic tetracarboxylic anhydride and their diimide derivatives were reported among the first n-channel materials. Among the materials of this class, perylenetetracarboxylic diimides having fluorinated side chains showed mobilities up to 0.72 $cm^2V^{-1}$ $s^{-1}$, which only slightly decreased upon air exposure. Air stability, packing grain size and morphology of the deposited films as well as electrical performance can be altered by varying side-chain length, insertion of oxygenated groups and degree of fluorination. However, most of the perylene building blocks, due to the structural rigidity and moderate solubility, do not allow readily structural changes limiting the volume of materials accessible.

Other classes of n-type organic materials have been described such as cyanovinyl oligomers, fullerenes.

J. Am. Chem. Soc. 2009, 131, 16616-16617 describes ambipolar charge transport properties of diketopyrrolopyrrole-copolymers.

A benzothiadiazole-diketopyrrolopyrrole copolymer described in Mater. 2010, 22, 47, 5409-5413, shows high and balanced hole- and electron mobilities of 0.35 $cm^2V^{-1}s^{-1}$ and 0.40 $cm^2V^{-1}s^{-1}$, respectively. Larger electron mobilities values up to 0.85 $cm^2V^{-1}s^{-1}$ were achieved in air for electron-only transporting n-type polymer, called poly{[N,N9-bis(2-octyldodecyl)-naphthalene-1,4,5,8-bis(dicarboximide)-2,6-diyl]-alt-5,59-(2,29-bithiophene)}, (Polyera Activink N2200), in a staggered top gate configuration.

N-type semiconductor materials consisting of oligothiophenes bearing fluorinated side groups have been also described in J. Am. Chem. Soc. 2005, 127, 1348 and Angew. Chem. Int. Ed. 2003, 42, 3900. These oligomers showed mobilities up to 0.43 $cm^2V^{-1}s^{-1}$. However, OFETs based on most of these perfluoroaryl and perfluoroalkylaryl substituted materials were unstable in air or suffered from high threshold voltage. Fluorocarbonyl-functionalized oligomers were also described, which showed improved air stability, but lower electron mobilities with respect to fluorinated oligomers.

Oligomers and polymers containing a bithiophene-imide units as inner core have also been described.

For example, J. Am. Chem. Soc. 2008, 130, 9679-9694 describes N-alkyl-2,2'-bithiophene-3,3'-dicarboximide-based homopolymers and copolymers showing p-type or n-type semiconductor behavior depending on the polymeric structure. However, no air-stable devices could be achieved with such materials. In addition, the poor reactivity of the starting dihalogenated bithiophene-imide compounds limits the accessibility of this class of materials.

J. Am. Chem. Soc. 1998, 120, 5355-5362, Tetrahedron Letters 44 (2003)1653-1565 disclose copolymers containing electron poor 3,4-imido-thienyl blocks alternated to electron rich amino substituted thienyl blocks. No investigation was performed regarding the electrical properties of such copolymers.

N-alkylated poly(dioxopirrolothiophene)s are described in Organic Letters 2004, 6, 19, 3381-3384. However, no proof of an efficient n-type behavior in OFET devices is reported.

Each of the afore mentioned class of materials has poor electrical performances.

WO2008/127029 relates to dioxypirrolo-heterocyclic compounds having the pyrrole moiety fused to the 3,4 position of the thienyl ring and organic electronic devices using said dioxypirrolo-heterocyclic compounds.

Wei Hong et al, "Linear fused dithieno[2,3-b: 3'2'-d] thiophene diimides" Organic Letters, vol 13, no. 6, 18 Mar. 2011, pages 1420-1413, discloses a class of linear fully fused dithieno thiophene diimides.

The documents: DE1954550; Ronova Iga A et al: "The effect of conformational rigidity on the initial decomposition temperature of some heterocyclic polyimides", High Performance Polymers, Institute of Physics Publishing, Bristol GB, vol. 14, No. 2, 1 Jan. 2002, pages 195-208; and Gaina C. et al, "Polyimides containing 1,4-dithiine units and their corresponding thiophene 2,3,4,5 tetracarboxylimide units" High Performance Polymers, Institute of physics publishing, Bristol GB, vol. 11, No. 2, 1 Jun. 1999, pages 185-195, disclose polymeric diimide compounds in which the member connecting the polymer repeating units is the N-imidic substituent. The three last cited documents do not mention any semiconductor property of the compounds therein disclosed.

WO2006/094292 discloses thienopyridine compounds capable of modulating the stability and/or activity of hypoxia inducible factor, pharmaceutical compositions comprising said compounds and chemical intermediates useful for preparing said compounds. Among said chemical intermediates, specific compounds having a 4,6-dioxo-thieno[2,3-c]pyrrole nucleus are disclosed.

EP0467206 discloses specific compounds having a 4,6-dioxo-thieno[2,3-c]pyrrole nucleus and their use as herbicide.

However, WO2006/094292 and EP0467206 do not teach the semiconductor properties of said compounds.

FIGS. 5a) and b) is a transfer saturation curve P type of a thin film transistor obtained with a compound of FIG. 1.

According to an aspect of the present invention, a compound of formula (I) or (II) is provided:

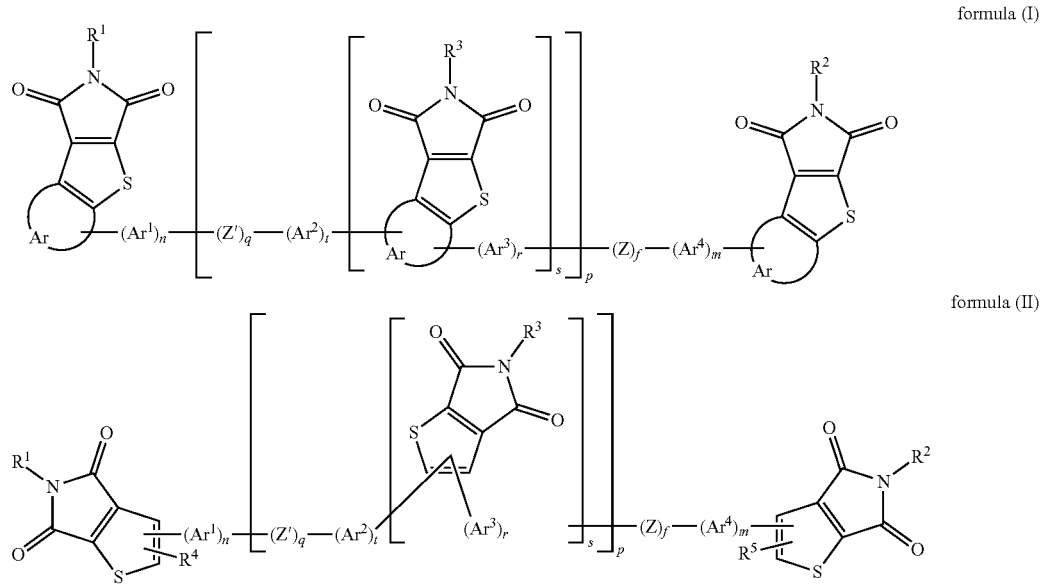

formula (I)

formula (II)

Therefore, there is still the need of n-type organic semiconductor materials or compounds that possess higher electron mobility properties.

In the present specification and in the claims, the term "n-type organic semiconductor" means a material that, inserted as active layer in a field effect device architecture with a source, a drain and gate control electrodes, shows an electron mobility higher than $10^{-7}$ cm$^2$V$^{-1}$s$^{-1}$.

It is an object of the present invention to provide new organic materials suitable for use as semiconductor material, which is free from said disadvantages. Said object is achieved with compounds whose main features are disclosed in the first claim, a use of said compounds whose main features are disclosed in claim 10 and an electronic device whose main features are disclosed in claim 12. Other features of said compounds are disclosed in claims 2 to 9.

Advantageously, the compounds according to the present invention may be useful as p-type, n-type or ambipolar organic semiconductor material.

Particularly, the compounds according to the present invention possess high electron mobility properties, excellent stability under atmospheric conditions and are accessible through synthetically easy processes.

Further advantages and features of the compounds, materials and devices according to the present invention will become clear to those skilled in the art from the following detailed and non-limiting description of an aspect thereof with reference to the attached drawings, wherein:

FIG. 1 are UV-vis and emission spectra of a compound according to the present invention;

FIGS. 2 a) and b) are DCS thermograms of the compound of FIG. 1;

FIGS. 3 a) and b) are lucous curves and output curves of a thin film transistor obtained with a compound of FIG. 1;

FIG. 4 is a transfer saturation curve N type of a thin film transistor obtained with a compound of FIG. 1;

wherein:

$R^1$, $R^2$, $R^3$ independently of each other, are selected in the group consisting of hydrogen, $C_1$-$C_{40}$ linear or branched alkyl groups, $C_2$-$C_{40}$ linear or branched alkenyl groups, $C_2$-$C_{40}$ linear or branched alkynyl groups, $C_1$-$C_{40}$ linear or branched heteroalkyl groups, $C_2$-$C_{40}$ linear or branched heteroalkenyl groups, $C_2$-$C_{40}$ linear or branched heteroalkynyl groups, $C_3$-$C_{40}$ linear or branched cycloalkyl groups, $C_2$-$C_{40}$ linear or branched heterocycloalkyl groups, $C_2$-$C_{40}$ linear or branched alkylcarboxylic groups, $C_2$-$C_{40}$ linear or branched alkylcarboxamide groups, $C_2$-$C_{40}$ linear or branched alkylimino groups, $C_1$-$C_{40}$ linear or branched alkylsulphonic groups, $C_1$-$C_{40}$ linear or branched nitrile groups, $C_6$-$C_{50}$ unsubstituted and substituted monocyclic aryl groups, $C_{10}$-$C_{50}$ polycyclic aryl groups, $C_{10}$-$C_{50}$ substituted polycyclic aryl groups, $C_1$-$C_{50}$ unsubstituted and substituted monocyclic heteroaryl groups, $C_6$-$C_{50}$ polycyclic heteroaryl groups, $C_6$-$C_{50}$ substituted polycyclic heteroaryl groups;

$R^4$ and $R^5$, independently of each other, are selected in the group consisting of hydrogen, halogens, $C_1$-$C_{20}$ linear or branched alkyl groups, $C_2$-$C_{20}$ linear or branched alkenyl groups, $C_2$-$C_{20}$ linear or branched alkynyl groups, $C_1$-$C_{20}$ linear or branched heteroalkyl groups, $C_2$-$C_{20}$ linear or branched heteroalkenyl groups, $C_2$-$C_{20}$ linear or branched heteroalkynyl groups, $C_3$-$C_{20}$ linear or branched cycloalkyl groups, $C_2$-$C_{20}$ linear or branched heterocycloalkyl groups, $C_2$-$C_{20}$ linear or branched alkylcarboxylic groups, $C_2$-$C_{20}$ linear or branched alkylcarboxamide groups, $C_2$-$C_{20}$ linear or branched alkylimino groups, $C_1$-$C_{20}$ linear or branched alkylsulphonic groups, $C_1$-$C_{20}$ linear or branched nitrile groups, Ar, $Ar^1$, $Ar^2$, $Ar^3$ and $Ar^4$, independently of each other, are moieties selected in the group consisting of a $C_6$-$C_{50}$ unsubstituted and substituted monocyclic aryl groups, $C_{10}$-$C_{50}$ polycyclic aryl groups, $C_{10}$-$C_{50}$ substituted polycyclic aryl groups, $C_1$-$C_{50}$ unsubstituted and substituted monocyclic heteroaryl groups, $C_6$-$C_{50}$ polycyclic heteroaryl groups, $C_6$-$C_{50}$ substituted polycyclic heteroaryl groups and combinations thereof as dimers, trimers and tetramers;

Z and Z', independently of each other, are selected in the group consisting of the bivalent radicals selected in the groups consisting of the formulas (III), (IV), (V), (VI), (VII), (VIII), (IX), (X):

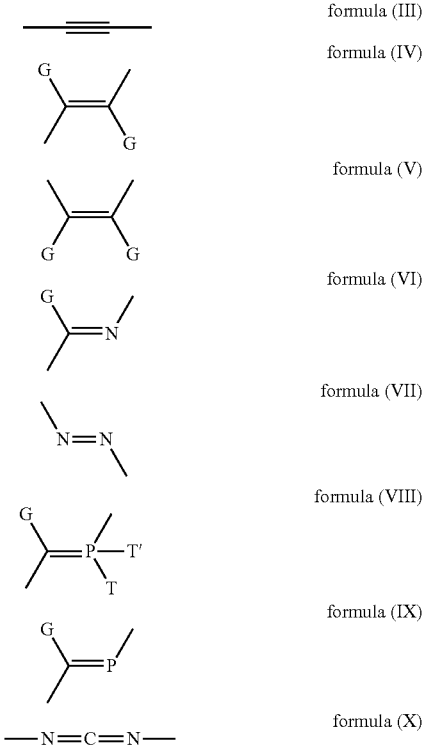

formula (III)

formula (IV)

formula (V)

formula (VI)

formula (VII)

formula (VIII)

formula (IX)

formula (X)

wherein G is selected among hydrogen, halogens, $C_1$-$C_{20}$ linear or branched alkyl groups, $C_2$-$C_{20}$ linear or branched alkenyl groups, $C_2$-$C_{20}$ linear or branched alkynyl groups, $C_1$-$C_{20}$ linear or branched heteroalkyl groups, $C_2$-$C_{20}$ linear or branched heteroalkenyl groups, $C_2$-$C_{20}$ linear or branched heteroalkynyl groups, $C_3$-$C_{20}$ linear or branched cycloalkyl groups, $C_2$-$C_{20}$ linear or branched heterocycloalkyl groups, $C_2$-$C_{20}$ linear or branched alkylcarboxylic groups, $C_2$-$C_{20}$ linear or branched alkylcarboxamide groups, $C_2$-$C_{20}$ linear or branched alkylimino groups, $C_1$-$C_{20}$ linear or branched alkylsulphonic groups, $C_1$-$C_{20}$ linear or branched nitrile groups, $C_6$-$C_{50}$ unsubstituted and substituted monocyclic aryl groups, $C_{10}$-$C_{50}$ polycyclic aryl groups, $C_{10}$-$C_{50}$ substituted polycyclic aryl groups, $C_1$-$C_{50}$ unsubstituted and substituted monocyclic heteroaryl groups, $C_6$-$C_{50}$ polycyclic heteroaryl groups, $C_6$-$C_{50}$ substituted polycyclic heteroaryl groups and combinations thereof;

T and T' are selected in the group consisting of $C_1$-$C_{20}$ linear or branched alkyl groups, $C_2$-$C_{20}$ linear or branched alkenyl groups, $C_2$-$C_{20}$ linear or branched alkynyl groups, $C_1$-$C_{20}$ linear or branched heteroalkyl groups, $C_2$-$C_{20}$ linear or branched heteroalkenyl groups, $C_2$-$C_{20}$ linear or branched heteroalkynyl groups, $C_3$-$C_{20}$ linear or branched cycloalkyl groups, $C_2$-$C_{20}$ linear or branched heterocycloalkyl groups, $C_2$-$C_{20}$ linear or branched alkylcarboxylic groups, $C_2$-$C_{20}$ linear or branched alkylcarboxamide groups, $C_2$-$C_{20}$ linear or branched alkylimino groups, $C_6$-$C_{50}$ unsubstituted and substituted monocyclic aryl groups, $C_{10}$-$C_{50}$ polycyclic aryl groups, $C_{10}$-$C_{50}$ substituted polycyclic aryl groups, $C_1$-$C_{50}$ unsubstituted and substituted monocyclic heteroaryl groups, $C_6$-$C_{50}$ polycyclic heteroaryl groups, $C_6$-$C_{50}$ substituted polycyclic heteroaryl groups and combinations thereof;

s is 0 or 1;

n, m, r and t, independently of each other, are integers between 1 and 50;

q and f, independently of each other, are integers between 1 and 10; and p is an integer between 0 and 5.

In the present description and in the claims:

a "heteroalkyl group" is intended to include, for example, a halogenoalkyl group, a hydroxyalkyl group, a alkoxyalkyl group;

a "heteroalkenyl group" is intended to include, for example, a halogenoalkenyl group, a hydroxyalkenyl group, a alkoxyalkenyl group;

a "heteroalkynyl group" is intended to include, for example, a halogenoalkynyl group, a hydroxyalkynyl group, a alkoxyalkynyl group.

In formulas (VII); (VIII); (IX) and (X), P is phosphor and N is nitrogen.

The value of p is preferably 0, 1 or 2.

The value of q and f, independently of each other, is preferably between 1 and 5; more preferably q and f are 1 or 2; even more preferably q and f are 1.

The values of n, m, r and t are preferably comprised between 2 and 50, more preferably between 2 and 30, even more preferably between 2 and 10.

When p assumes the values of 0, then n is particularly preferably comprised between 2 and 50, more preferably between 2 and 30, even more preferably between 2 and 10.

According to an embodiment of the invention, s is 0 and p is 1 or 2.

According to another embodiment of the invention, s is 0, p is 1 or 2 and n, q, f, m are 1.

Preferably, G is selected in the group consisting of hydrogen, bromine, chlorine, iodine, methyl, ethyl, vinyl, propyl, i-propyl, allyl, propenyl, hexyl, methoxyl, ethoxyl, hexyloxyl, ethylamine, butylamine, hexylamine.

In formula (V) and (VIII) the two G groups and/or the G group and one of the T/T' group may also be connected to form together with the double bond, a cycle, for example cyclohexene, cyclopentene, dihydropyrrole, phosphranylidene as shown in the following formulas (Va), (Vb), (Vc) that are specific embodiments of formula (V), and formula (VIIIa) which is a specific embodiment of formula (VIII):

formula (Va)

formula (Vb)

formula (Vc)

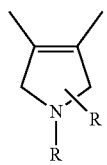

formula (VIIIa)

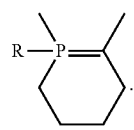

In an embodiment of the present invention, the groups Z and Z' are selected in the group consisting of ethynylene cis-ethenylene and trans-ethenylene.

Preferably, $R^4$ and $R^5$ are hydrogen.

Preferably, according to the present invention, $R^1$, $R^2$ and $R^3$ are selected in the group consisting $C_1$-$C_8$ alkyl groups, $C_2$-$C_8$ alkenyl groups, $C_2$-$C_8$ alkynyl groups, phenyl group, substituted phenyl groups, benzyl group, substituted benzyl groups.

Preferably, according to the present invention Ar, $Ar^1$, $Ar^2$, $Ar^3$ and $Ar^4$, independently of each other, are selected in the group consisting of a $C_6$-$C_{20}$ unsubstituted and substituted monocyclic aryl groups, $C_{10}$-$C_{20}$ polycyclic aryl groups, $C_{10}$-$C_{50}$ substituted polycyclic aryl groups, $C_1$-$C_{20}$ unsubstituted and substituted monocyclic heteroaryl groups, $C_6$-$C_{20}$ polycyclic heteroaryl groups, $C_6$-$C_{20}$ substituted polycyclic heteroaryl groups and combinations thereof as dimers, trimers and tetramers The preferred substituents of said monocyclic aryl groups, polycyclic aryl groups, monocyclic heteroaryl groups, polycyclic heteroaryl groups of Ar, Ar', $Ar^e$, $Ar^3$ and $Ar^4$, are selected among halogens, alkyl, alkenyl, alkynyl or heteroalkyl groups. More preferably, said substituent groups are selected in the group consisting of linear or branched $C_1$-$C_{12}$ alkyl, linear or branched $C_2$-$C_{12}$ alkenyl, linear or branched $C_2$-$C_{12}$ alkynyl, $C_1$-$C_{12}$ perfluoroalkyl, $C_1$-$C_{12}$ oxyalkyl, $C_1$-$C_{12}$ aminoalkyl, $C_1$-$C_{12}$ thioalkyl, $C_1$-$C_{12}$ haloalkyl, $C_2$-$C_{12}$ carboxyalkyl groups, $C_1$-$C_{12}$ silicioalkyl groups.

According to an aspect of the present invention, the compounds of following formulas (Ia) and (IIa) are provided, which correspond to those of formulas (I) and (II), wherein p is equal to 0:

formula (Ia)

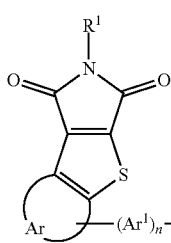 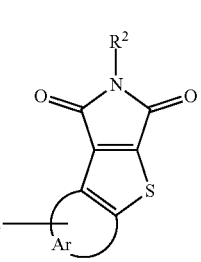

formula (IIa)

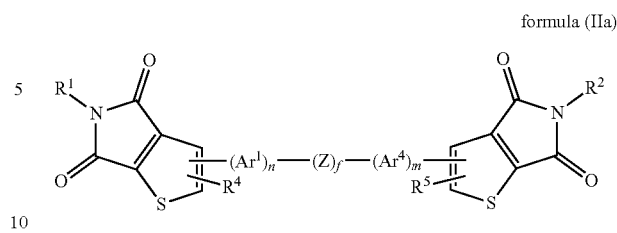

wherein $R^1$, $R^2$, $R^4$, $R^5$, Ar, $Ar^1$, $Ar^4$, Z, f, n, m are as above defined.

In the present description and in the claims, the curved lines in formulas (I), (Ia), connecting the Ar moiety to the thieno(bis)imide unit, indicate that said Ar moiety forms a fused ring system with said thieno(bis)imide unit.

In addition, as usual in chemical drawing practice, in the present description and in the claims the bond lines crossing the thiophene double bond in formulas (II), (IIa), indicates that the $(Ar^1)_n$ and $(Ar^4)_m$ moiety may be bound to any of the 2 or 3 position in the thiophene rings and are not fused thereto. Preferably, the $(Ar^1)_n$ and $(Ar^4)_m$ moieties are bound to the 2 position of the thiophene rings.

In formulas (I) and (Ia), the $(Ar^1)_n$ and $(Ar^4)_m$ moieties may be bound to any position of the Ar moiety that is fused to the thieno(bis)imide unit.

In formulas (Ia) and (Ha) the integers n and m are preferably comprised between 1 and 30, more preferably between 2 and 30, even more preferably between 2 and 10.

Preferably, in the formulas (Ia) and (IIa), $R^4$ and $R^5$ are hydrogen and f is 1 or 2.

The compounds according to the invention wherein n is 2 are characterized by an advantageously high solubility in a number of solvents, for example dichloromethane, dimethyl sulfoxide, tetrahydrofuran, allowing for high level purification and easy solution processing.

Preferably, the $Ar^1$, $Ar^2$, $Ar^3$, $Ar^4$, independently f each other, are units selected among the following groups (a), (b), (c), (d), (e), (f), (g), (h), (i), (l), (m), (n), (o), (p), (q), (r):

(a)

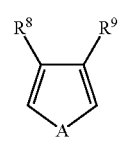

(b)

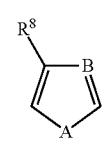

(c)

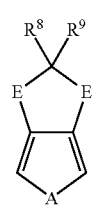

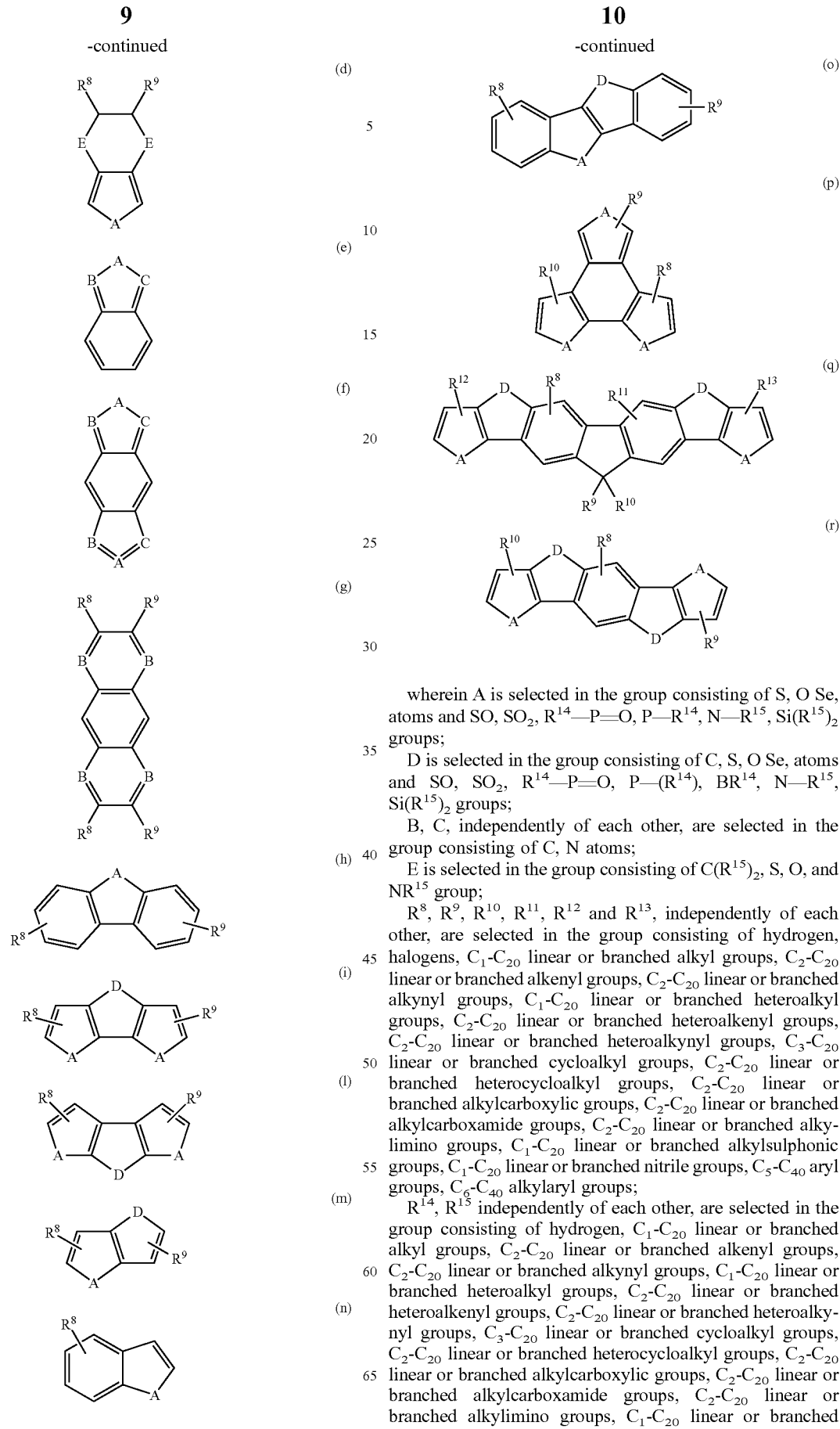

wherein A is selected in the group consisting of S, O Se, atoms and SO, $SO_2$, $R^{14}$—P=O, P—$R^{14}$, N—$R^{15}$, $Si(R^{15})_2$ groups;

D is selected in the group consisting of C, S, O Se, atoms and SO, $SO_2$, $R^{14}$—P=O, P—($R^{14}$), $BR^{14}$, N—$R^{15}$, $Si(R^{15})_2$ groups;

B, C, independently of each other, are selected in the group consisting of C, N atoms;

E is selected in the group consisting of $C(R^{15})_2$, S, O, and $NR^{15}$ group;

$R^8$, $R^9$, $R^{10}$, $R^{11}$, $R^{12}$ and $R^{13}$, independently of each other, are selected in the group consisting of hydrogen, halogens, $C_1$-$C_{20}$ linear or branched alkyl groups, $C_2$-$C_{20}$ linear or branched alkenyl groups, $C_2$-$C_{20}$ linear or branched alkynyl groups, $C_1$-$C_{20}$ linear or branched heteroalkyl groups, $C_2$-$C_{20}$ linear or branched heteroalkenyl groups, $C_2$-$C_{20}$ linear or branched heteroalkynyl groups, $C_3$-$C_{20}$ linear or branched cycloalkyl groups, $C_2$-$C_{20}$ linear or branched heterocycloalkyl groups, $C_2$-$C_{20}$ linear or branched alkylcarboxylic groups, $C_2$-$C_{20}$ linear or branched alkylcarboxamide groups, $C_2$-$C_{20}$ linear or branched alkylimino groups, $C_1$-$C_{20}$ linear or branched alkylsulphonic groups, $C_1$-$C_{20}$ linear or branched nitrile groups, $C_5$-$C_{40}$ aryl groups, $C_6$-$C_{40}$ alkylaryl groups;

$R^{14}$, $R^{15}$ independently of each other, are selected in the group consisting of hydrogen, $C_1$-$C_{20}$ linear or branched alkyl groups, $C_2$-$C_{20}$ linear or branched alkenyl groups, $C_2$-$C_{20}$ linear or branched alkynyl groups, $C_1$-$C_{20}$ linear or branched heteroalkyl groups, $C_2$-$C_{20}$ linear or branched heteroalkenyl groups, $C_2$-$C_{20}$ linear or branched heteroalkynyl groups, $C_3$-$C_{20}$ linear or branched cycloalkyl groups, $C_2$-$C_{20}$ linear or branched heterocycloalkyl groups, $C_2$-$C_{20}$ linear or branched alkylcarboxylic groups, $C_2$-$C_{20}$ linear or branched alkylcarboxamide groups, $C_2$-$C_{20}$ linear or branched alkylimino groups, $C_1$-$C_{20}$ linear or branched alkylsulphonic groups, $C_1$-$C_{20}$ linear or branched nitrile groups, $C_5$-$C_{40}$ aryl groups, $C_6$-$C_{40}$ alkylaryl groups.

In formulas (h), (i), (l), (m), (n), (o), (p), (q), (r), it is meant that the substituent group may be bound to any position of any ring forming the delocalized system.

Examples of the above described groups of formula (a)-(r) are the following:

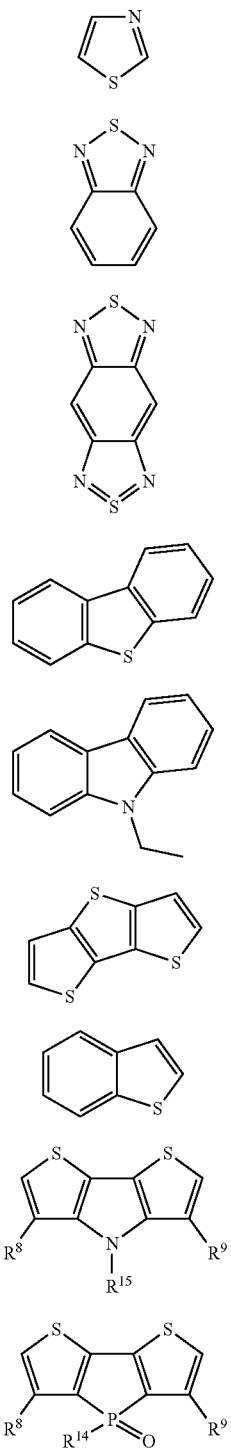

In other preferred embodiments of the present invention, the $Ar^1$, $Ar^2$, $Ar^3$, $Ar^4$ groups may be a dimer comprising a thiophene, thiazole, furane, benzodithiazole, thienothiophene or phenyl unit that is linked to another aryl unit, such as the above represented (a)-(r) groups, like in the following formulas (s) and (t):

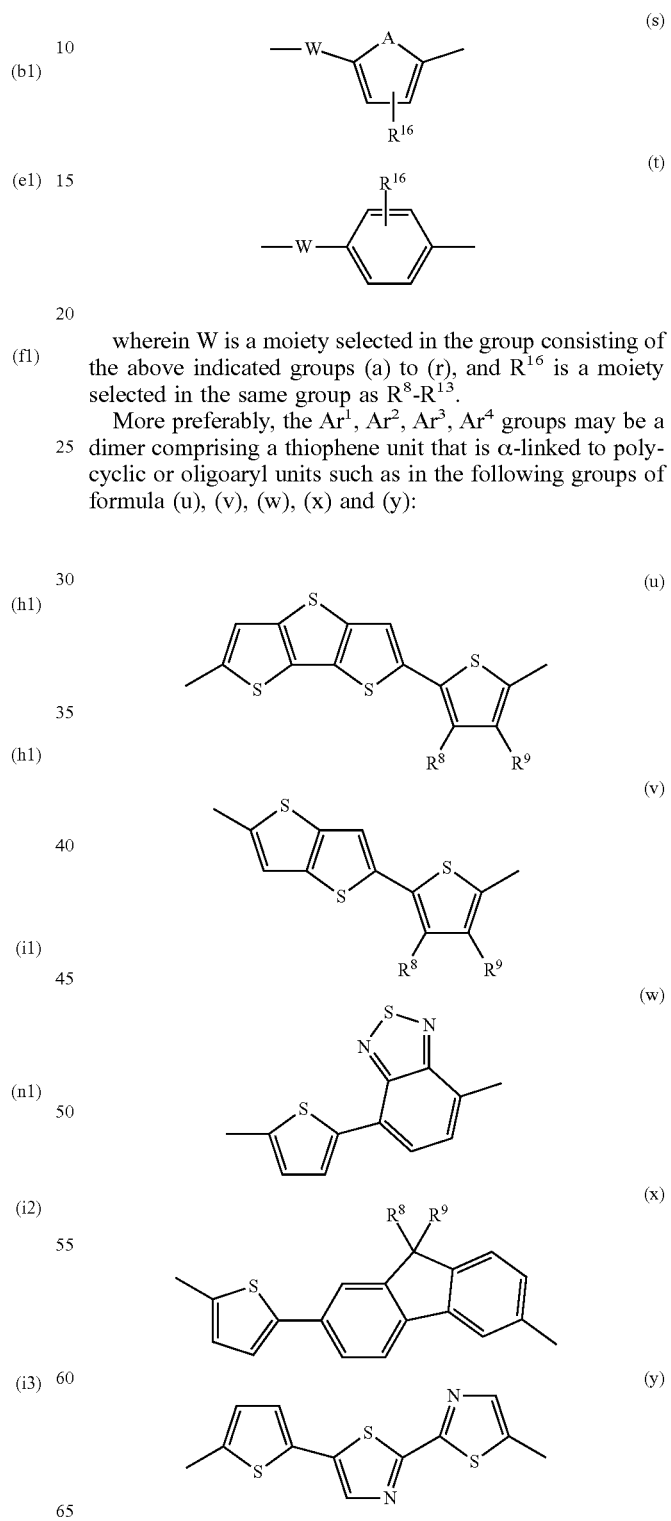

wherein W is a moiety selected in the group consisting of the above indicated groups (a) to (r), and $R^{16}$ is a moiety selected in the same group as $R^8$-$R^{13}$.

More preferably, the $Ar^1$, $Ar^2$, $Ar^3$, $Ar^4$ groups may be a dimer comprising a thiophene unit that is α-linked to polycyclic or oligoaryl units such as in the following groups of formula (u), (v), (w), (x) and (y):

wherein $R^8$, $R^9$ and n have the above described meanings.

In an embodiment of the invention, Ar¹, Ar², Ar³, Ar⁴ are thiophene units or substituted thiophene units.

The Ar moiety fused to the thienoimide unit of the compounds of formulas (I) and (Ia) according to the present invention may be advantageously formed of one, two or three aromatic rings.

Preferably, in formulas (I), (Ia), Ar is selected in the group consisting of the following rings (α), (β), (γ), (δ), (∈), (ζ), (η), (θ), (ι):

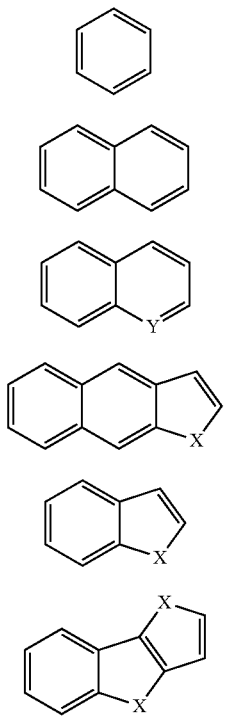

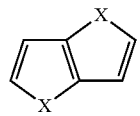

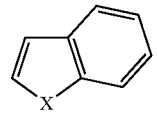

wherein X is selected in the group consisting of S, SO, $SO_2$, O, Si, Se, $NR^{17}$, Y is selected in the group consisting of C and N;

$R^{17}$ is selected in the group consisting of hydrogen, $C_1$-$C_{20}$ linear or branched alkyl groups, $C_2$-$C_{20}$ linear or branched alkenyl groups, $C_2$-$C_{20}$ linear or branched alkynyl groups, $C_1$-$C_{20}$ linear or branched heteroalkyl groups, $C_2$-$C_{20}$ linear or branched heteroalkenyl groups, $C_2$-$C_{20}$ linear or branched heteroalkynyl groups, $C_3$-$C_{20}$ linear or branched cycloalkyl groups, $C_2$-$C_{20}$ linear or branched heterocycloalkyl groups, $C_2$-$C_{20}$ linear or branched alkylcarboxylic groups, $C_2$-$C_{20}$ linear or branched alkylcarboxamide groups, $C_2$-$C_{20}$ linear or branched alkylimino groups, $C_1$-$C_{20}$ linear or branched alkylsulphonic groups, $C_1$-$C_{20}$ linear or branched nitrile groups, $C_5$-$C_{40}$ aryl groups, $C_6$-$C_{40}$ alkylaryl groups.

Specific examples of compounds of formula (I) and (II) according to the present invention are for example the following synthesized compounds:

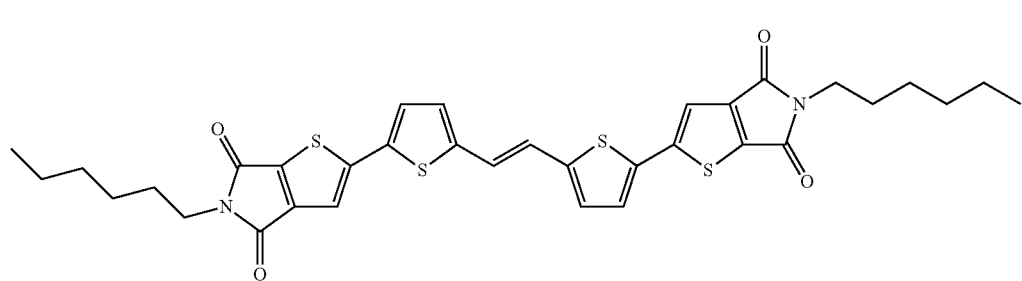

compound 1

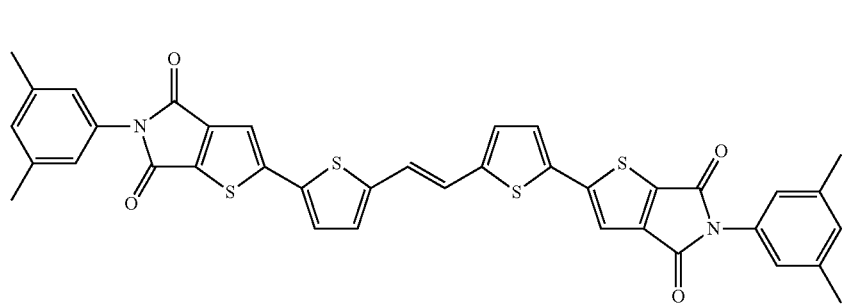

compound 2

-continued compound 3

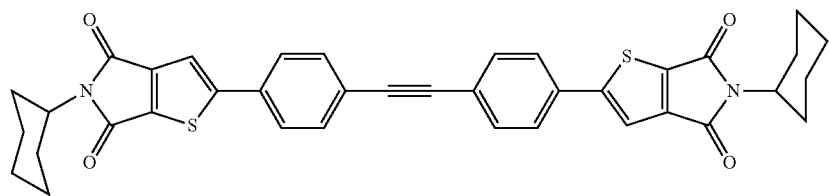

compound 4

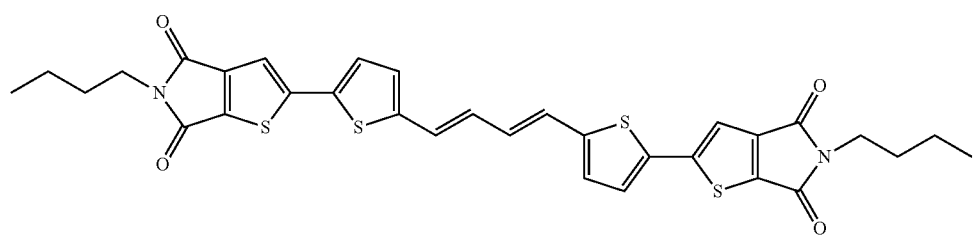

compound 5

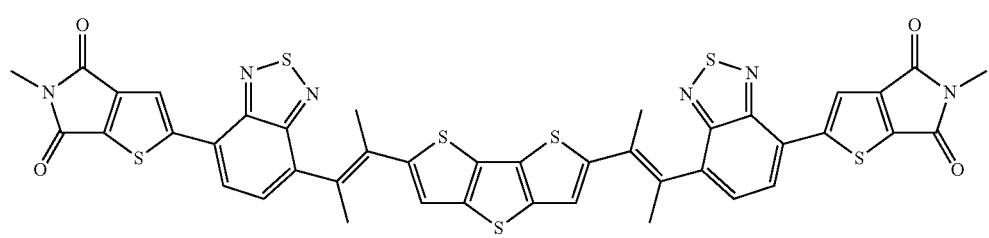

compound 6

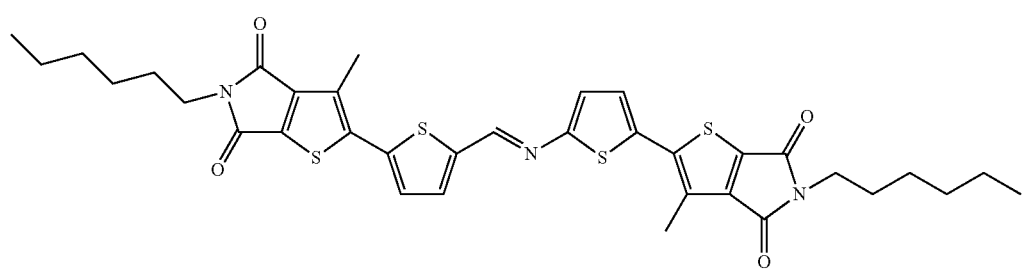

comound 7

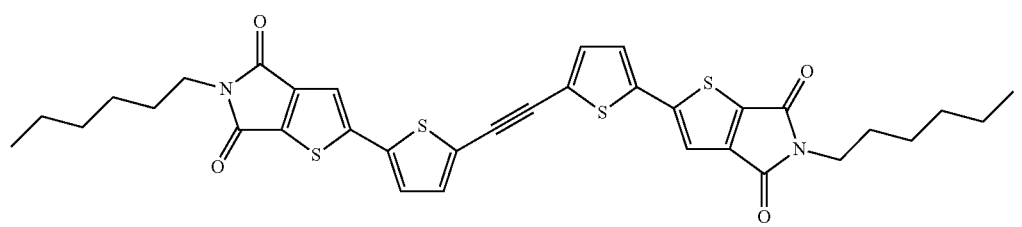

compound 8

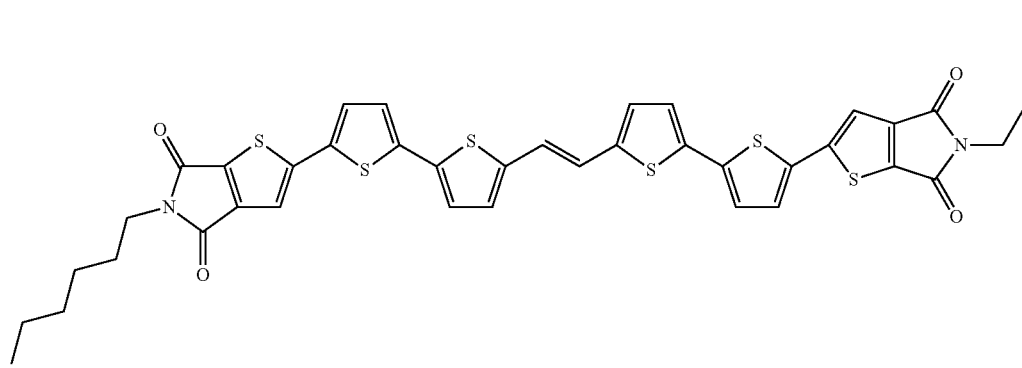

Without wishing to limit the present invention to any theory, it is believed that the thienoimide moiety, due to its strong electrowithdrawing effect, can increase the overall electron affinity of p-conjugated materials promoting the electron charge transport capability. The presence of the unsaturated bond as linker between thienoimide p-conjugated blocks can promotes high solubility, can allow for the fine tuning of the HOMO-LUMO energy levels, can promote high molecular planarity thus improved self-assembly and crystalline morphology, ultimately enhancing the electrical properties and device responses.

On the other hand, the opposite terminal groups may be exploited to tune the dipole moment, the HOMO LUMO energy levels and orbital distribution and the packing modality, this ultimately influencing the functional properties of the resulting materials.

Among the main advantages of such compounds with respect to other classes of n-type materials are to be mentioned the easy accessibility and structural versatility.

The thienoimide moiety can be coupled to selected π-conjugated cores by cross-couplings under conventional or microwave-assisted methods as described below.

The easy accessibility of the compounds according to the invention also allows an easy modification of the oligomer size, and degree and type of molecular functionalization, which in turn permits application fine property-specific design toward the targeted applications.

The compounds according to the present invention can be obtained with electronic level of purity by chromatography, crystallization and sublimation, with unambiguous molecular structure determination through classic analytical methods.

Contrarily to the thiophene-3,4-imide polymers, bithiophene-imide polymers and perylene tetracarboxylic diimide systems according to the prior art, this class of materials can be prepared with high reproducibility from batch to batch, which is crucial to achieve devices with reproducible responses.

According to still another aspect of the invention, it is provided a process for the production of a compound according to the invention, wherein the process comprises reiterative halogenation of aromatic compounds and cross-coupling reactions. The thieno(bis)imide building block can be halogenated or metallated to undergo cross-coupling reactions with aromatic ($Ar^2$ or $Ar^3$) and/or unsaturated (Z) based counterparts or to dimer of Ar and Z moieties (i.e. $Ar^2$—Z). The processes according to the present invention are preferably catalized by palladium.

A process for the production of a compound according to formula (Ia) is schematized in scheme 1, whereas scheme 2 shows a possible production process of compounds of formula (IIa):

Scheme 1

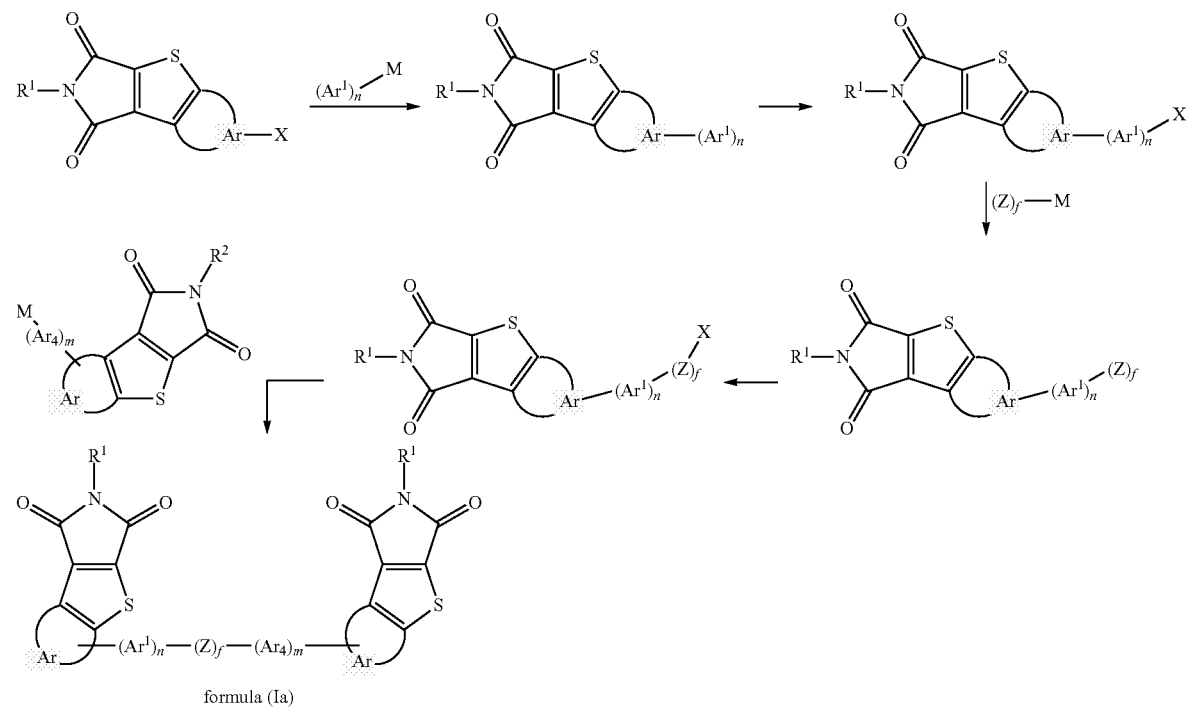

formula (Ia)

Scheme 2

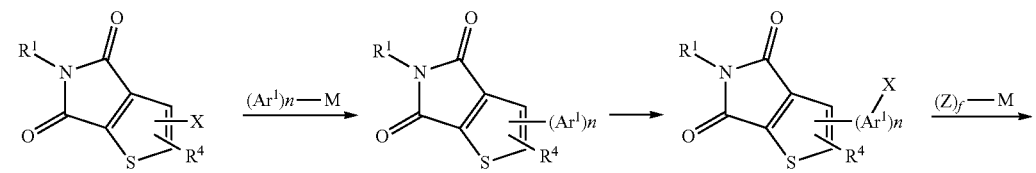

X = halogen
M = organometallic compound

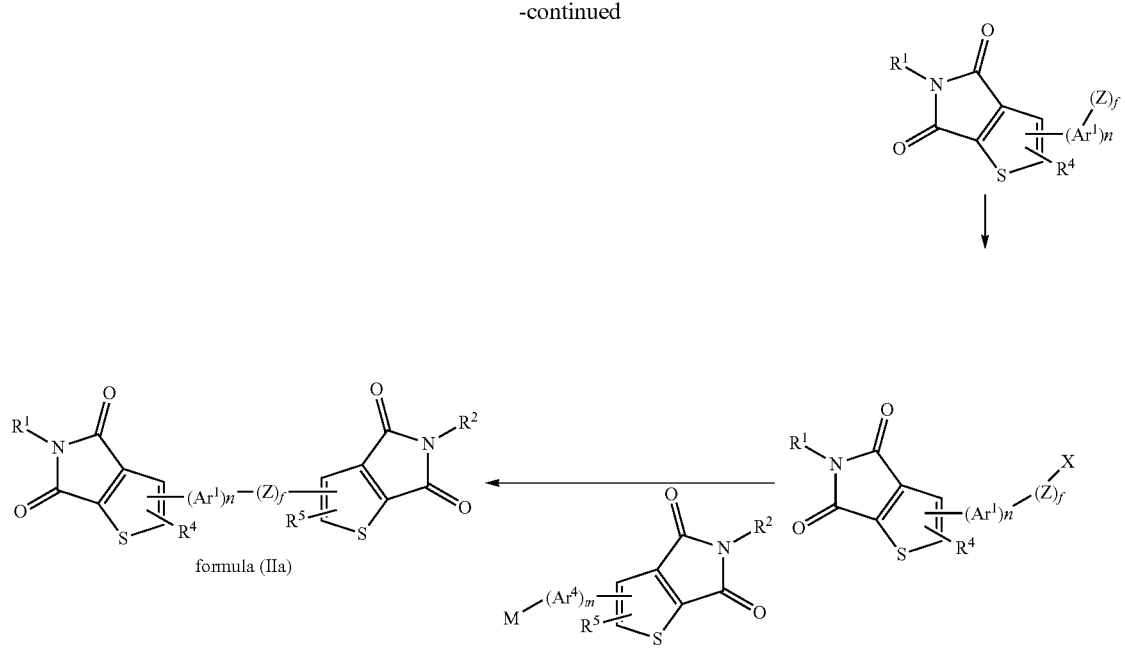

formula (IIa)

In schemes 1 and 2, X is an halogen atom, such as Br, I; M is an organometal compound such as $B(OR')_2$ and $SnR''_3$, wherein R' is hydrogen or an alkyl moiety and R" is an alkyl moiety.

In another aspect thereof, the present invention relates to a semiconductor material, comprising at least one compound according to formulas (I) and/or (II). Preferably, said semiconductor material comprises at least one compound according to formulas (Ia) and/or (IIa).

In an embodiment thereof, said semiconductor material comprises compounds 1.

According to another aspect, the invention relates to an electronic device comprising a semiconductor layer in contact with a number of electrodes, wherein the semiconductor layer includes at least one compound according to formulas (I) and/or (II). Preferably, said semiconductor layer comprises at least one compound according to formulas (Ia) and/or (IIa). More preferably, said semiconductor layer comprises compound 1.

Preferably, said electronic device comprising a semiconductor layer including the compounds according to the present invention is selected among optical devices, electrooptical devices, field effect transistors, integrated circuit, thin film transistors, organic light-emitting devices, and organic solar cells.

Particularly, thin films of the thienoimide based materials according to the invention can be used as active layers in OFETs and OLET devices as demonstrated in the following examples. They can be used as electron- or hole-transporting layer or ambipolar semiconductor in single layer OFET, as multifunctional electron- and hole-transporting and light emitting layer in single layer OLET, and as hole or electron transporting layer in multi-layer OLET.

Finally, applications of compounds and materials according to the present invention in organic photovoltaics can be envisaged.

In the following examples, all $^1H$, $^{13}C$, spectra were recorded at room temperature on a Varian Mercury 400 spectrometer operating at 400 MHz ($^1H$) and 100.6 MHz ($^{13}C$). Chemical shifts were calibrated using the internal $CDCl_3$ resonance which were referenced to TMS.

Mass spectra were collected on an ion trap Finningan Mat GCQ spectrometer operating in electron impact (EI) ionization mode. Each sample was introduced to the ion source region of the GCQ via a direct exposure probe (DEP).

Melting points were determined on a 'hot-stage' apparatus where the melting process was observed with the aid of a microscope.

UV-Vis spectra were recorded using a Perkin Elmer Lambda 20 spectrometer. Photoluminescence spectra were obtained with a Perkin Elmer LS50B spectrofluorometer using an excitation wavelength corresponding to the maximum absorption lambda.

Differential Scanning calorimetry (DSC) analysis were performed by using a Thass DSC-XP-10 instrument under atmospheric conditions.

UV-Vis spectra were recorded using a Perkin Elmer Lambda 20 spectrophotometer. Photoluminescence spectra were collected on a Perkin Elmer LS50 spectrofluorometer.

EXAMPLE 1

Synthesis of (E)-2,2'-(5,5'-(ethene-1,2-diyl)bis(thiophene-5,2-diyl))bis(5-hexyl-4H-thieno[2,3-c]pyrrole-4,6(5H)-dione, compound 1

Step (a)

2-(5-bromothiophen-2-yl)-5-hexyl-4H-thieno[2,3-c]pyrrole-4,6(5H)-dione was prepared from commercially available thiophene-2,3-dicarboxylic acid following the procedure described in M. Melucci, M. Zambianchi, L. Favaretto, M. Gazzano, A. Zanelli, M. Monari, R. Capelli, S. Troisi, S. Toffanin, M. Muccini, Chem. Commun. 2011, 47, 11840 by using n-hexyl amine instead of n-butyhilamine in the same molar ratio.

Step (b)

Scheme 3. Synthetic route to compound 1

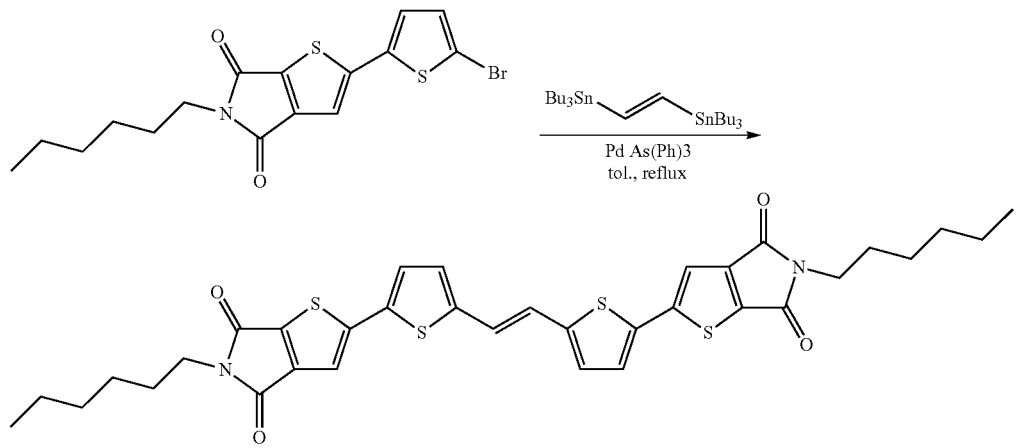

To a refluxing toluene solution (8 ml) of 2-(5-bromothiophen-2-yl)-5-hexyl-4H-thieno[2,3-c]pyrrole-4,6(5H)-dione (175 mg, 0.44 mmol) and in-situ prepared catalyst Pd(AsPh$_3$)$_4$ (10 mol %, i.e. 11 mg of Pd$_2$dba$_3$ and 26 mg of AsPh$_3$) under N$_2$ atmosphere, commercially available trans-1,2-bis(tributylstannyl)ethene (153 mg, 0.20 mmol) in toluene (3 ml), was added drop wise. The solution was refluxed for 24 h then the solvent was removed under vacuum, and the crude product was washed with pentane. The residue was purified by flash chromatography performed on a automated system (CombiFlash® Rf 200, Teledyne-Isco, Lincoln, Nebr., USA) using a 4-gram silica RediSep column and cyclohexane-ethyl acetate solvent gradients. The fractions containing the product were combined, the solvent evaporated, and the residue crystallized from hot toluene to give a dark red solid (81 mg, 58%). M.p. 255° C., MS (70 eV, EI): m/z 662 (M.$^{-1}$), absorption maximum, 465 nm, emission maximum, 588 nm in DCM; $^1$H NMR (CDCl$_3$, TMS/ppm) δ 7.31 (s, 2H), 7.24 (d, $^3$J=4.0 Hz, 2H), 7.04 (d, $^3$J=4.0 Hz, 2H), 7.02 (s, 2H), 3.60 (t, 4H), 1.64 (m, 4H), 1.31 (m, 12H), 0.88 (m, 6H); $^{13}$C NMR (CDCl$_3$, TMS/ppm) δ 163.9, 162.7, 149.8, 145.2, 143.6, 137.3, 134.3, 128.0, 126.6, 122.0, 116.4, 38.6, 31.4, 28.8, 26.5, 22.5, 14.0. Anal. Calcd for C$_{34}$H$_{34}$N$_2$O$_4$S$_4$ (662.90): C, 61.60; H, 5.17. Found: C, 61.54; H, 5.22.

FIG. 1 shows the UV-vis and emission spectra of compound 1 in CH$_2$Cl$_2$.

The DSC thermograms of compound 1 (second run, 25° C./min) in air are shown in FIGS. 3 (a) and (b).

The heating curve (FIG. 2a) shows a first transition located at about 220° C. corresponding to the melting of the crystalline phase to the liquid crystalline phase and a second transition corresponding to the clearing point at about 240° C. On cooling the melt (FIG. 2b), a transition was observed at about 190° C. and corresponds to the re-crystallization of the melt.

In polarized microscopy images, the liquid crystalline mesophases were observed between 240° C. and 242° C. when heating a compound 1 powder sample.

EXAMPLE 2

Fabrication and Optoelectronic Measurements of Thin Film Transistor (OTFT)

Organic thin film transistors were fabricated in bottom gate-top contact geometry. An ITO substrate was cleaned be means of two sonication cycles, first in acetone and then 2-isopropanol, for 10 minutes each. Then a 450 nm thick dielectric layer of PMMA was grown by spin-coating on top of the clean ITO substrate. The relative electric permittivity ϵ was 3.6 at 100 Hz. The PMMA layer was then thermally annealed in a glove box at 120° C. (i.e., around 10° C. above the glass transition temperature for PMMA) for 15 hours under inert atmosphere. (CPMMA=7.08 nF/cm$^2$).

Then, an organic thin film layer consisting of compound 1 was grown on the top of said dielectric layer by vacuum sublimation in a vacuum chamber, with a deposition rate of 0.03 Å/s, at a base pressure of 10$^{-6}$ mbar. The substrate temperature during the film deposition was kept at room temperature (RT).

Then, gold drain and source electrodes were made on top of the organic thin film by evaporation through a shadow mask. The thickness of said gold drain and source electrodes was 50 nm, while the channel length (L) and the channel width (W) were 40 µm and 12 mm, respectively.

The electrical characteristics of such a transistor were then measured. All optoelectronic measurements were carried out in an MBraun nitrogen glove box using a standard SUSS Probe Station.

The mobility values in saturation were calculated from the locus curves using the standard equations:

$$\mu = L/(W*C)A^2 \qquad [\text{eq. 1}]$$

wherein A is the angular coefficient of the line fitting the square root of the drain current vs the applied voltage, L is the channel length, W the channel width and C is the transistor dielectric capacitance.

FIG. 3 (a) shows the locus curve N, and FIG. 3(b) the type output curve of such transistor comprising an organic layer consisting of compound 1.

Figure 1:
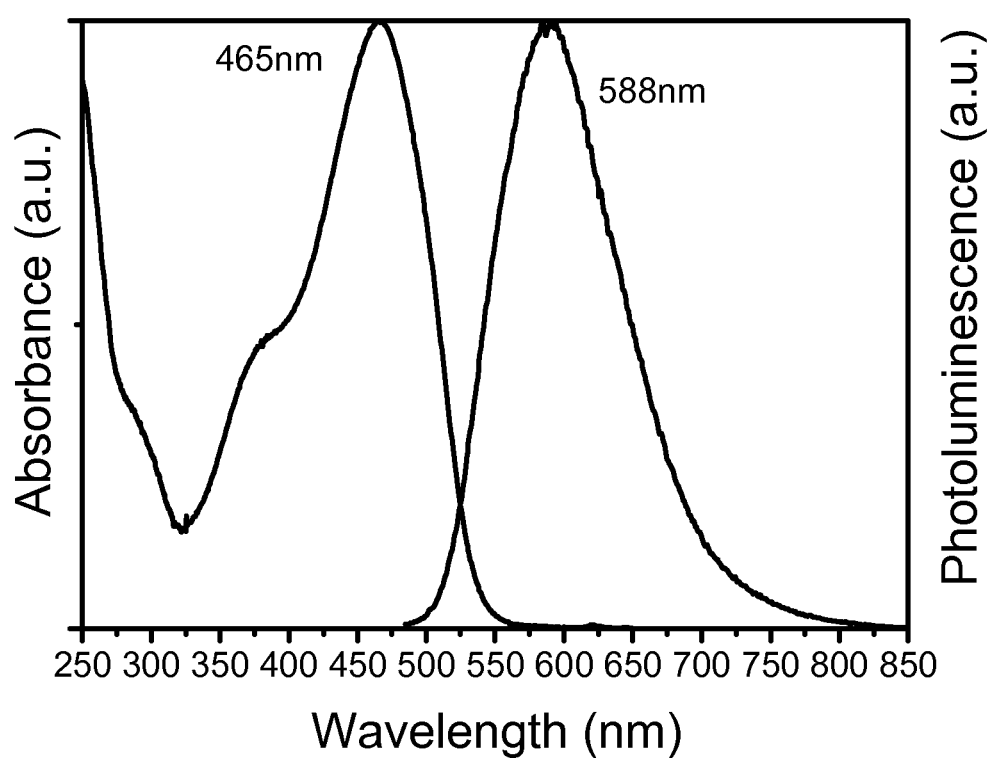
Figure 2:
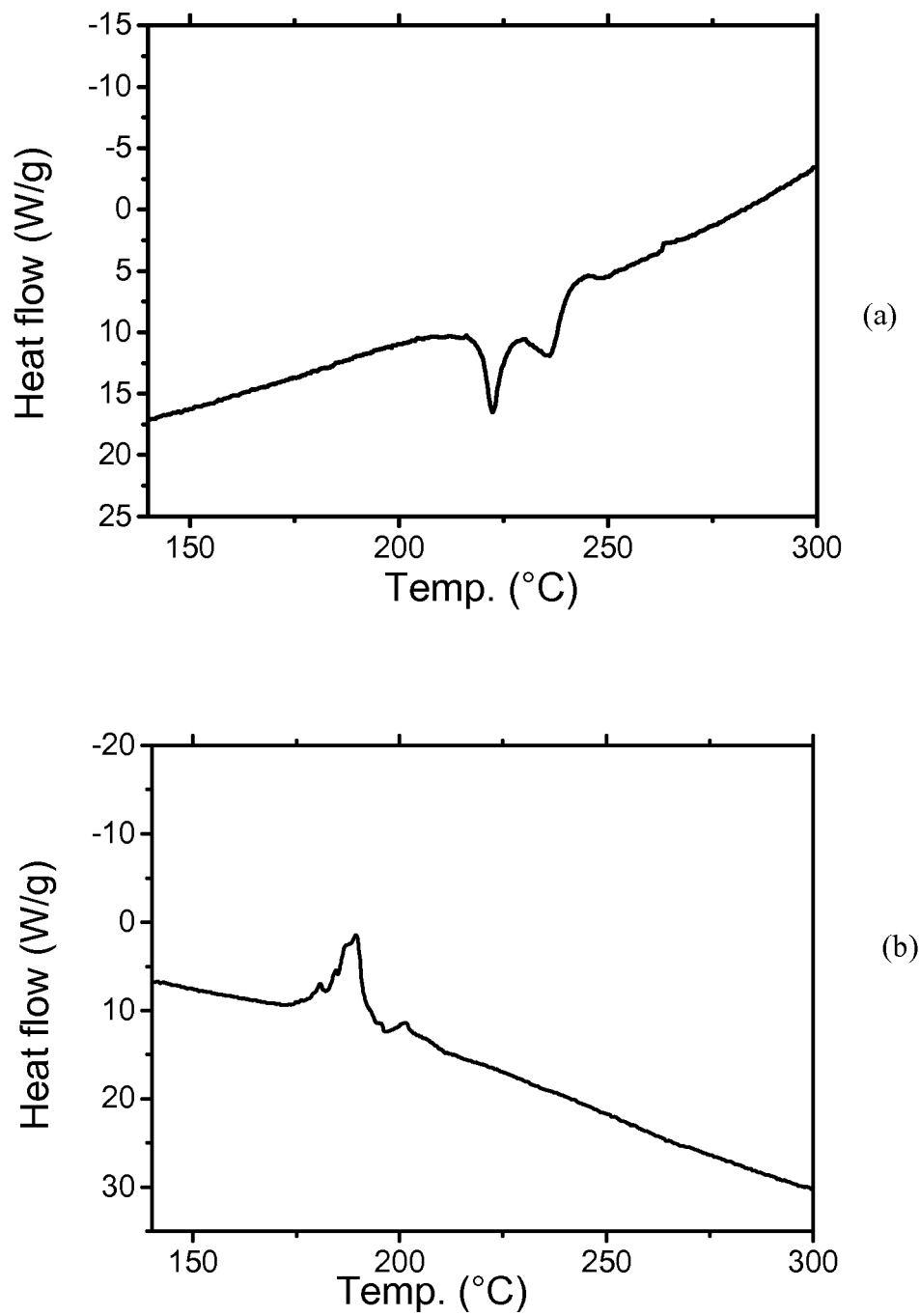
Figure 4:
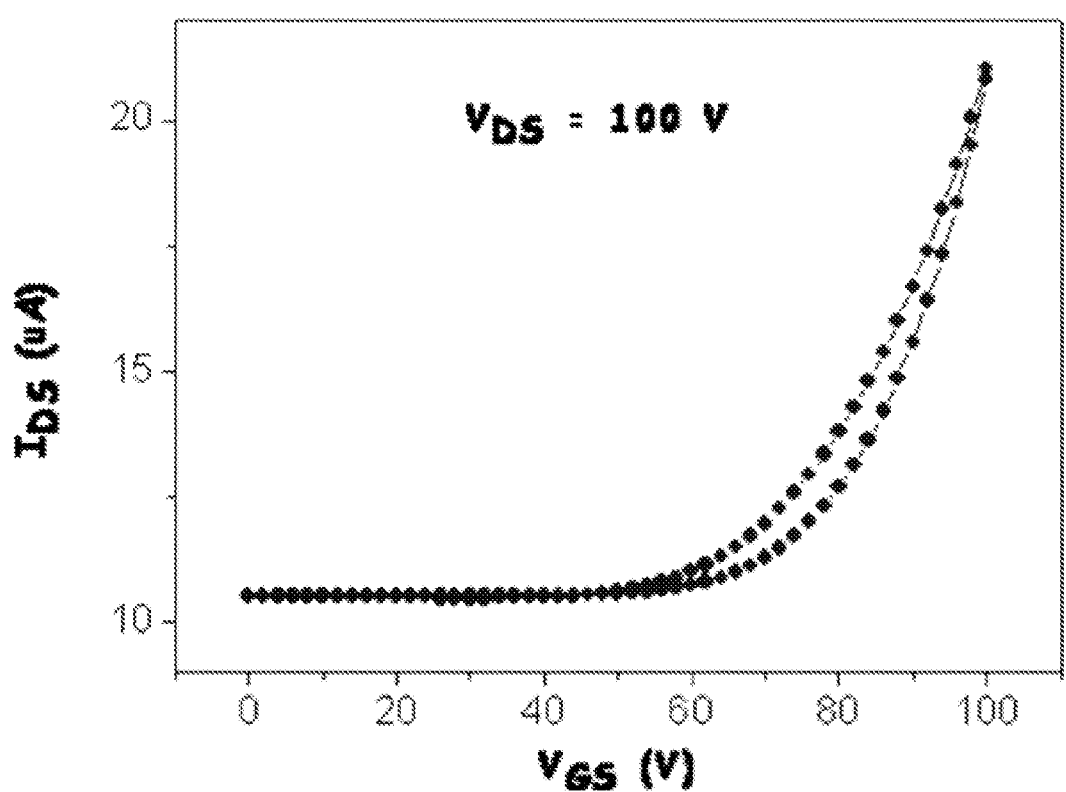
FIG. 4 shows the transfer saturation curve N Type of such transistor comprising an organic layer consisting of compound 1, with $\mu_N$=2 10$^{-3}$ cm$^2$/Vs, $V_T^N$≈60V.
Figure 5A:
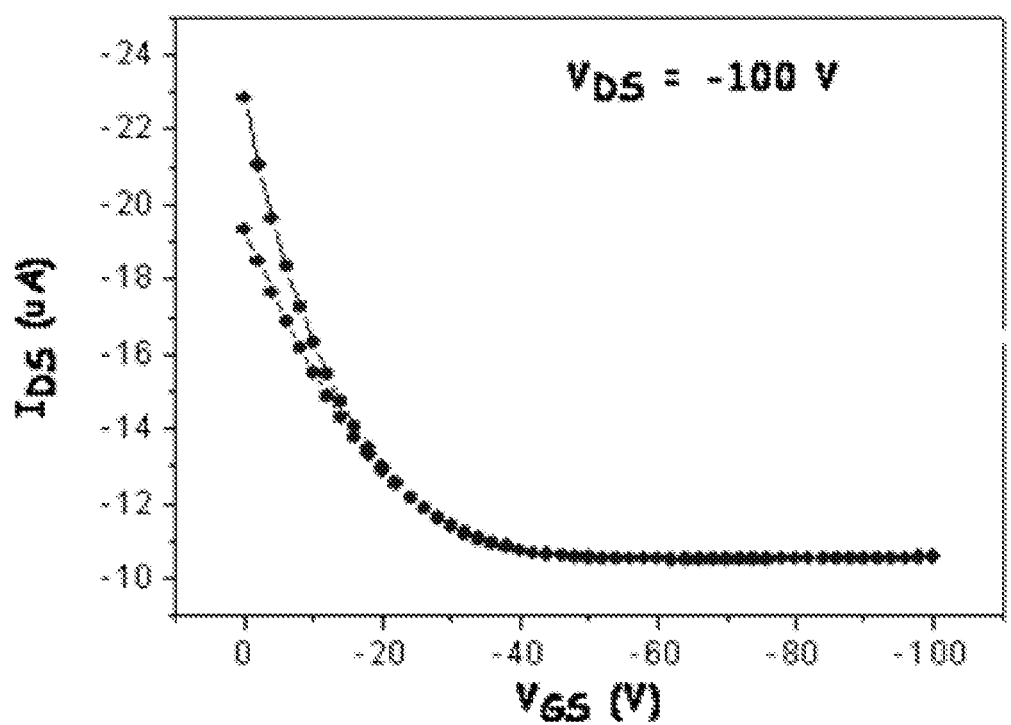
Figure 5B:
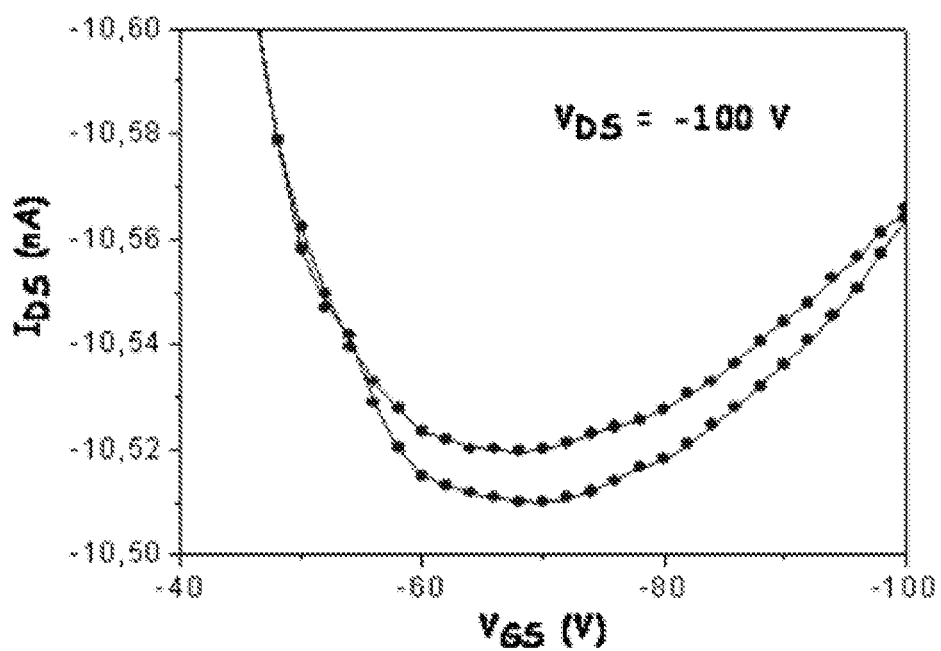

FIG. 5 shows the transfer saturation curve P Type of such transistor comprising an organic layer consisting of compound 1, with $\mu_P = 1 \cdot 10^{-7}$ cm$^2$/V/s, $V_T^P \approx 70$V.

EXAMPLE 3

Synthesis of 2,2'-(5,5'-(Ethyne-1,2-diyl)bis(thiophene-5,2-diyl))bis(5-hexyl-4H-thieno[2,3-c]pyrrole-4,6(5H)-dione), compound 7

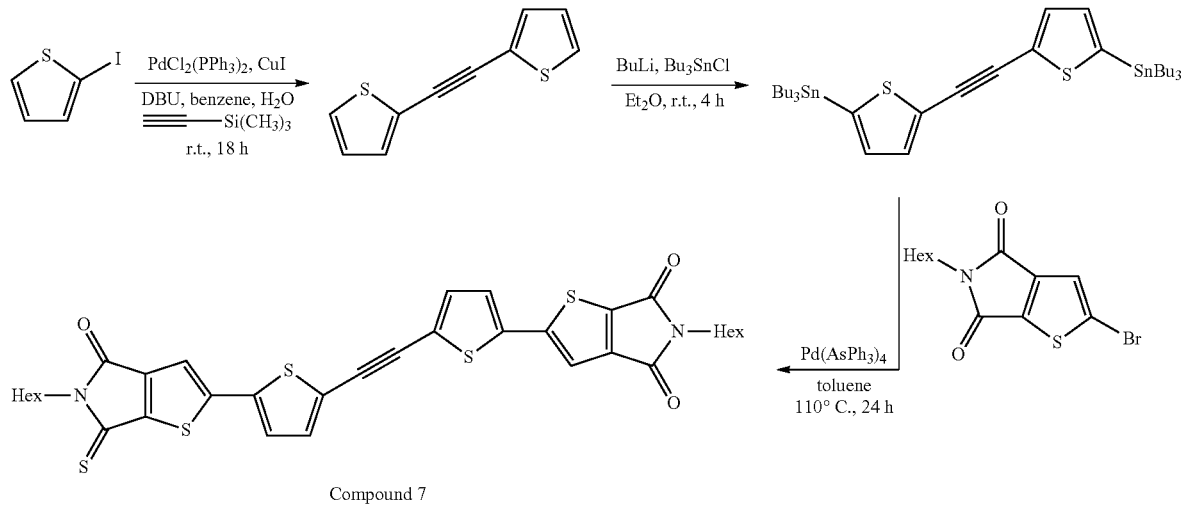

Compound 7

Step a): Synthesis of 2,2'-Bithienylacethylene

A dry round-bottom flask was charged with PdCl$_2$(PPh$_3$)$_2$ (210 mg, 6 mol %), CuI (190 mg, 10 mol %), and 2-iodothiophene, (1.02 ml, 0.01 mol). Dry benzene (50 ml) was added under stirring. Argon-sparged DBU (8.97 ml, 0.06 mol) was added by syringe and the reaction flask was purged with argon. Ice-chilled trimethylsilylethynylene (0.69 ml, 5 mmol) was added by syringe, immediately followed by distilled water (73 µL, 4 mmol). The reaction was carried out in absence of light for 18 h at room temperature. The reaction mixture was then partitioned in ethyl ether and distilled water (200 ml each). The organic layer was washed with aq HCl (10% w/w, 3×250 ml) and brine (1×250 ml), dried over Na$_2$SO$_4$ and concentrated under reduced pressure. Purification of the crude by flash-chromatography on silica gel (elution with n-hexane) gave the pure product 2,2'-bithienylacethylene as a white crystalline solid. Yield=72% (984 mg). M.p. 101° C. (lit. 96° C.). ELMS m/z 190 (M$^+$). $^1$H NMR (CDCl$_3$, TMS/ppm) δ 7.31 (dd, $^3$J=5.2 Hz, $^4$J=1.2 Hz, 2H), 7.28 (dd, $^3$J=3.6 Hz, $^4$J=1.2 Hz, 2H), 7.02 (dd, $^3$J=5.2 Hz, $^3$J=3.6 Hz, 2H); $^{13}$C NMR (CDCl$_3$, TMS/ppm) δ 132.1, 127.6, 127.1, 122.9, 86.2.

Step b): Synthesis of 5,5'-Bis(tributylstannyl)-2,2'-bithienylacethylene

To a solution of 2,2'-bithienylacethylene (190 mg, 1.00 mmol) in dry ethyl ether (12 mL) n-BuLi (2.5 M in hexane, 0.92 ml, 2.30 mmol) was added at room temperature. After 1 h, tributyltin chloride (0.57 ml, 2.10 mmol) was added dropwise. The reaction mixture was left under stirring at room temperature for 4 h, then partitioned in AcOEt and distilled water (50 ml each). The organic layer was washed with brine (2×50 ml), dried over Na$_2$SO$_4$ and concentrated. The title compound was obtained in quantitative yield as a yellow-amber oil and used without further purification for the final synthetic step. EI-MS m/z 768 (M$^+$). $^1$H NMR (CDCl$_3$, TMS/ppm) δ 7.36 (d, $^3$J=3.2 Hz, 2H), 7.05 (d, $^3$J=3.2 Hz, 2H), 1.55 (m, 12H), 1.33 (m, 12H), 1.12 (m, 12H), 0.91 (m, 18H).

Step c): Synthesis of 2,2'-(5,5'-(Ethyne-1,2-diyl)bis(thiophene-5,2-diyl))bis(5-hexyl-4H-thieno[2,3-c] pyrrole-4,6(5H)-dione), compound 7

To a refluxing toluene solution (15 ml) of 2-bromo-5-hexyl-4H-thieno[2,3-c]pyrrole-4,6(5H)-dione, 4 (348 mg, 1.10 mmol) and in-situ prepared catalyst Pd(AsPh$_3$)$_4$ (10 mol %, i.e. 52 mg of Pd$_2$dba$_3$ and 122 mg of AsPh$_3$) under N$_2$ atmosphere, compound 3 (384 mg, 0.50 mmol) was added dropwise. The solution was refluxed for 24 h, then the solvent was removed under vacuum, and the crude product was washed with pentane. The residue was purified by flash chromatography performed on a automated system (CombiFlash® Rf 200, Teledyne-Isco, Lincoln, Nebr., USA) with a 24-gram silica RediSep column and cyclohexane-ethyl acetate solvent gradients.

Due to its strong retention on silica gel, the title compound was finally eluted with hot toluene. The fractions containing the product were combined, the solvent evaporated, and the residue crystallized from toluene giving 225 mg of orange solid (68% yield). M.p. 228° C. EI-MS m/z 660 (M$^+$). $\lambda_{max}$ (CH$_2$Cl$_2$), 433 nm, $\lambda_{em}$ (CH$_2$Cl$_2$), 547 nm. $^1$H NMR (CDCl$_3$, TMS/ppm) δ 7.34 (s, 2H), 7.25 (d, $^3$J=4.0 Hz, 2H), 7.24 (d, $^3$J=4.0 Hz, 2H), 3.60 (t, 4H), 1.62 (m, 4H), 1.31 (m, 12H), 0.88 (m, 6H). $^{13}$C NMR (CDCl$_3$, TMS/ppm) δ 163.8, 162.6, 148.9, 145.2, 138.1, 137.1, 133.5, 125.9, 124.0, 117.1, 88.1, 38.7, 31.4, 28.7, 26.5, 22.5, 14.0. Anal. Calcd for C$_{34}$H$_{32}$N$_2$O$_4$S$_4$ (660.89): C, 61.79; H, 4.88. Found: C, 61.72; H, 4.95.

EXAMPLE 4

Synthesis of (E)-2,2'-(5',5'''-(ethene-1,2-diyl)bis([2,2'-bithiophene]-5',5-diyl))bis(5-hexyl-4H-thieno[2,3-c]pyrrole-4,6(5H)-dione), compound 8

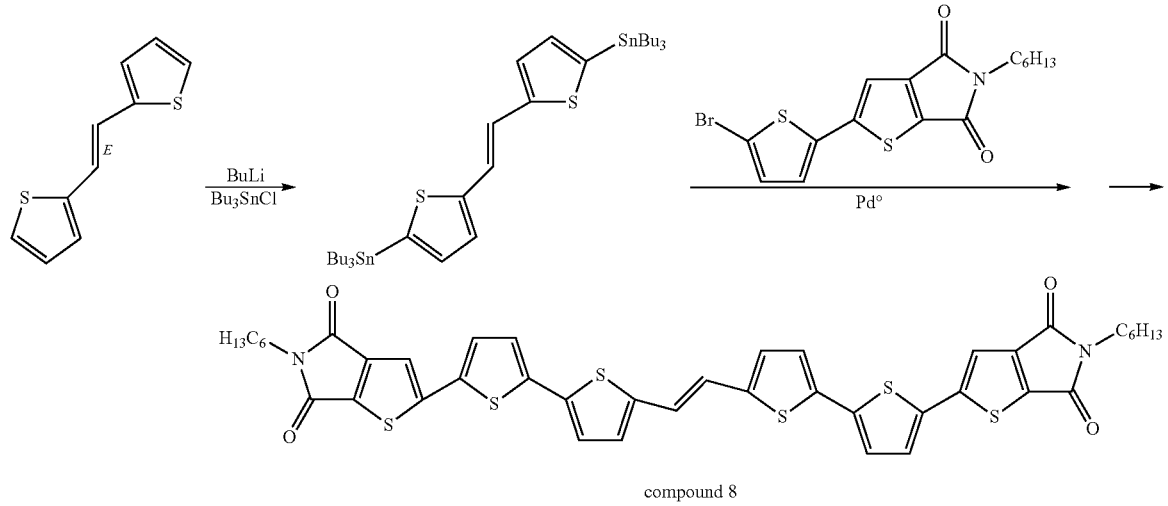

compound 8

Step a): Synthesis of (E)-1,2-bis(5-(tributylstannyl)thiophen-2-yl)ethane

To an anhydrous solution of (E)-1,2-bis(2-thienyl)ethane[ref 1] (0.900 g, 0.00469 mol) in 25 ml of THF under nitrogen atmosphere, TMEDA (Tetramethylethylenediamine) (0.0103 mol) was added at −50° C. Then, the solution was refrigerated at −78° C. and BuLi (2.5 M in hexane) (4.3 ml, 0.01078 mol) was added dropwise. The mixture was stirred for 30 minutes then refluxed for 1 hour and refrigerated at −78° C. At this temperature $Bu_3SnCl$ (3.2 g, 0.0098 mol) was added dropwise and the reaction mixture was stirred overnight at room temperature. The solvent was removed under vacuum, then the mixture was dissolved in $CH_2Cl_2$ and quenched with water. After extraction, the organic phase was dried over $Na_2SO_4$ and the solvent was evaporated, obtaining the desired compound as a brown oil (3.5 g, yield 98%).

EI-MS m/z 770 (M.$^+$).

$^1$H NMR (CDCl$_3$, TMS/ppm) δ 7.12 (d, $^3J$=3.6 Hz, 2H), 7.10 (s, 2H), 7.04 (d, $^3J$=3.2 Hz, 2H), 1.56 (m, 6H), 1.32 (m, 6H), 1.10 (m, 6H), 0.91 (t, 9H).

$^{13}$C NMR (CDCl$_3$, TMS/ppm) δ 148.2, 136.7, 136.0, 126.9, 121.1, 28.9, 27.3, 13.7, 10.8.

Ref 1: Heteroatom Chemistry, vol 14, n 3, 2003, 218.

Step b): Synthesis of (E)-2,2'-(5',5'''-(ethene-1,2-diyl)bis([2,2'-bithiophene]-5',5-diyl))bis(5-hexyl-4H-thieno[2,3-c]pyrrole-4,6(5H)-dione), compound 8

To a refluxing toluene solution (5 ml) of the compound obtained in step a) (163 mg, 0.41 mmol) and in-situ prepared catalyst Pd(AsPh$_3$)$_4$ (10 mol %, i.e. 21 mg of Pd$_2$dba$_3$ and 49 mg of AsPh$_3$ in 12 ml toluene) under N$_2$ atmosphere, 2 (145 mg, 0.188 mmol) in toluene (1.5 ml), was added dropwise. The solution was refluxed for 7 h then, at room temperature, pentane was added. The solid obtained by removing the solvents was purified by flash chromatography on silica gel (elution with pentane: CH$_2$Cl$_2$: AcOEt/40:30:30→pentane: CH$_2$Cl$_2$/70:30→CH$_2$Cl$_2$). The fractions containing the product were combined, the solvent evaporated, and the residue crystallized from hot toluene to give a dark red solid (65 mg, yield 42%).

M.p. 286° C. EI-MS m/z 826 (M.$^+$). $\lambda_{max}$ (CH$_2$Cl$_2$), 487 nm, $\lambda_{em}$ (CH$_2$Cl$_2$), 626 nm. $^1$H NMR (CDCl$_3$, TMS/ppm) δ 7.31 (s, 2H), 7.25 (d, $^3J$=3.6 Hz, 2H), 7.14 (d, $^3J$=4.0 Hz, 2H), 7.13 (d, $^3J$=3.6 Hz, 2H), 6.99 (d, $^3J$=4.0 Hz, 2H), 6.98 (s, 2H), 3.60 (t, 4H), 1.64 (m, 4H), 1.31 (m, 12H), 0.88 (t, 6H).

The invention claimed is:

1. A compound having formula (II):

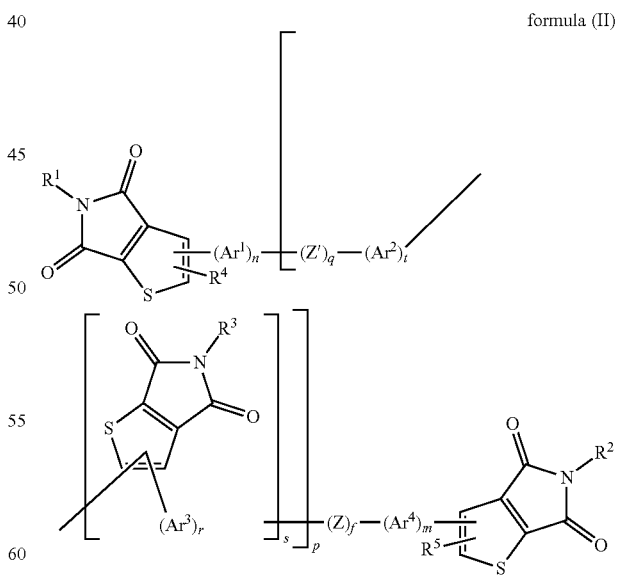

formula (II)

wherein:

$R^1$, $R^2$, $R^3$ independently of each other, are selected from a group consisting of $C_1$-$C_6$ linear alkyl groups, $C_6$ cycloalkyl groups, and $C_6$ unsubstituted and substituted monocyclic aryl groups;

R$^4$ and R$^5$, independently of each other, are selected from a group consisting of hydrogen, and C$_1$ alkyl group, Ar$^1$, Ar$^2$, Ar$^3$ and Ar$^4$, independently of each other, are moieties selected from a group consisting of a C$_6$ unsubstituted and substituted monocyclic aryl groups, C$_4$ unsubstituted and substituted monocyclic heteroaryl groups, and C$_6$ unsubstituted and substituted polycyclic heteroaryl groups or combinations thereof as dimers, trimers and tetramers;

Z and Z', independently of each other, are selected from a group consisting of bivalent radicals of formulas (III), (IV), (V), and (VI):

formula (III)

formula (IV)

formula (V)

formula (VI)

wherein G is selected from a group consisting of hydrogen, halogens, C$_1$-C$_{20}$ linear or branched alkyl groups, C$_2$-C$_{20}$ linear or branched alkenyl groups, C$_2$-C$_{20}$ linear or branched alkynyl groups, C$_1$-C$_{20}$ linear or branched heteroalkyl groups, C$_2$-C$_{20}$ linear or branched heteroalkenyl groups, C$_2$-C$_{20}$ linear or branched heteroalkynyl groups, C$_3$-C$_{20}$ linear or branched cycloalkyl groups, C$_3$-C$_{20}$ linear or branched heterocycloalkyl groups, C$_2$-C$_{20}$ linear or branched alkylcarboxylic groups, C$_2$-C$_{20}$ linear or branched alkylcarboxamide groups, C$_2$-C$_{20}$ linear or branched alkylimino groups, C$_1$-C$_{20}$ linear or branched alkylsulphonic groups, C$_1$-C$_{20}$ linear or branched nitrile groups, C$_6$-C$_{50}$ unsubstituted and substituted monocyclic aryl groups, C$_{10}$-C$_{50}$ polycyclic aryl groups, C$_{10}$-C$_{50}$ substituted polycyclic aryl groups, C$_1$-C$_{50}$ unsubstituted and substituted monocyclic heteroaryl groups, C$_6$-C$_{50}$ polycyclic heteroaryl groups, and C$_6$-C$_{50}$ substituted polycyclic heteroaryl groups or combinations thereof;

s is 0 or 1;

n, m, r and t, independently of each other, are integers between 1 and 50;

q and f, independently of each other, are integers between 1 and 10; and p is 0.

2. The compound according to claim 1, having formula (IIa):

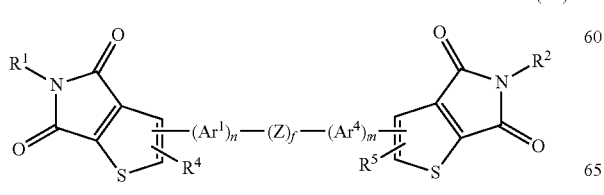

formula (IIa)

wherein R$^1$, R$^2$, R$^4$, R$^5$, Ar$^1$, Ar$^4$, Z, f, n, m are as specified in claim 1.

3. The compound according to claim 1, wherein q and f are each 1 or 2, and n, and m are between 2 and 10.

4. The compound according to claim 1, wherein Z' and/or Z are selected from a group consisting of ethynylene, cis-ethenylene and trans-ethenylene.

5. The compound according to claim 1, wherein Ar$^1$, Ar$^2$, Ar$^3$ and/or Ar$^4$, independently of each other, are selected from a group consisting of the following units (a), (b), (c), (d), (e), (f), (g), (h), (i), (l), (m), (n), (o), (p), (q), and (r):

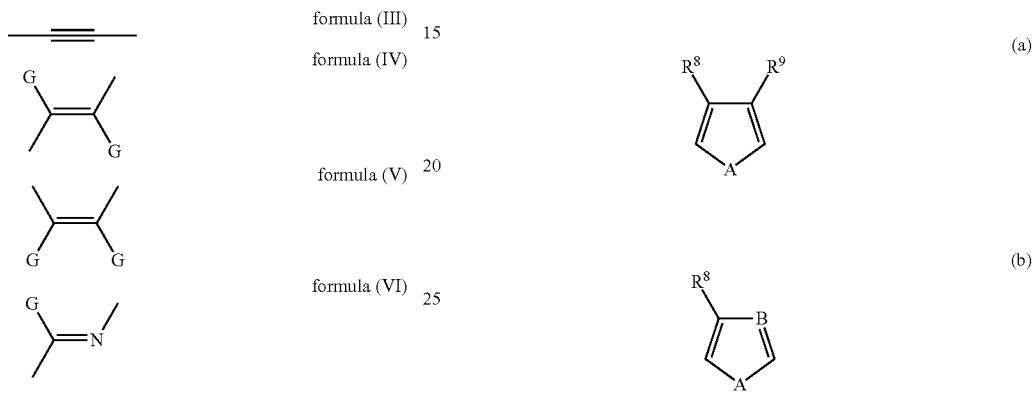

wherein A is selected from a group consisting of S, O, Se, atoms and SO, SO$_2$, R$^{14}$—P=O, P—R$^{14}$, N—R$^{15}$, Si(R$^{15}$)$_2$) groups;

D is selected from a group consisting of C, S, O Se, atoms and SO, SO$_2$, R$^{14}$—P=O, P—R$^{14}$, BR$^{14}$, N—R$^{15}$, Si(R$^{15}$)$_2$ groups;

B, C, independently of each other, are selected from a group consisting of C, N atoms;

E is selected from a group consisting of C(R$^{15}$)$_2$, S, O, and NR$^{15}$ group;

R$^8$, R$^9$, R$^{10}$, R$^{11}$, R$^{12}$ and R$^{13}$, independently of each other, are selected from a group consisting of hydrogen, halogens, C$_1$-C$_{20}$ linear or branched alkyl groups, C$_2$-C$_{20}$ linear or branched alkenyl groups, C$_2$-C$_{20}$ linear or branched alkynyl groups, C$_1$-C$_{20}$ linear or branched heteroalkyl groups, C$_2$-C$_{20}$ linear or branched heteroalkenyl groups, C$_2$-C$_{20}$ linear or branched heteroalkynyl groups, C$_3$-C$_{20}$ linear or branched cycloalkyl groups, C$_2$-C$_{20}$ linear or branched heterocycloalkyl groups, C$_2$-C$_{20}$ linear or branched alkylcarboxylic groups, C$_2$-C$_{20}$ linear or branched alkylcarboxamide groups, C$_2$-C$_{20}$ linear or branched alkylimino groups, C$_1$-C$_{20}$ linear or branched alkylsulphonic groups, C$_1$-C$_{20}$ linear or branched nitrile groups, and C$_5$-C$_{40}$ aryl groups, C$_6$-C$_{40}$ alkylaryl groups;

R$^{14}$, R$^{15}$ independently of each other, are selected from a group consisting of hydrogen, C$_1$-C$_{20}$ linear or branched alkyl groups, C$_2$-C$_{20}$ linear or branched alkenyl groups, C$_2$-C$_{20}$ linear or branched alkynyl groups, C$_1$-C$_{20}$ linear or branched heteroalkyl groups, C$_2$-C$_{20}$ linear or branched heteroalkenyl groups, C$_2$-C$_{20}$ linear or branched heteroalkynyl groups, C$_3$-C$_{20}$ linear or branched cycloalkyl groups, C$_3$-C$_{20}$ linear or branched heterocycloalkyl groups, C$_2$-C$_{20}$ linear or branched alkylcarboxylic groups, C$_2$-C$_{20}$ linear or branched alkylcarboxamide groups, C$_2$-C$_{20}$ linear or branched alkylimino groups, C$_1$-C$_{20}$ linear or branched alkylsulphonic groups, C$_1$-C$_{20}$ linear or branched nitrile groups, C$_5$-C$_{40}$ aryl groups, and C$_6$-C$_{40}$ alkylaryl groups.

6. The compound according to claim 1, wherein Ar$^1$, Ar$^2$, Ar$^3$ and/or Ar$^4$, independently of each other, are selected from a group consisting of the following groups (s) and (t):

wherein A is selected from a group consisting of S, O, Se, atoms and SO, $SO_2$, $R^{14}$—P=O, P—$R^{14}$, N—$R^{15}$, $Si(R^{15})_2$ groups;

W is a moiety selected from a group consisting of the units (a), (b), (c), (d), (e), (f), (g), (h), (i), (l), (m), (n), (o), (p), (q), and (r) of claim 5; and $R^{16}$ is selected from a group consisting of hydrogen, halogens, $C_1$-$C_{20}$ linear or branched alkyl groups, $C_2$-$C_{20}$ linear or branched alkenyl groups, $C_2$-$C_{20}$ linear or branched alkynyl groups, $C_1$-$C_{20}$ linear or branched heteroalkyl groups, $C_2$-$C_{20}$ linear or branched heteroalkenyl groups, $C_2$-$C_{20}$ linear or branched heteroalkynyl groups, $C_3$-$C_{20}$ linear or branched cycloalkyl groups, $C_3$-$C_{20}$ linear or branched heterocycloalkyl groups, $C_1$-$C_{20}$ linear or branched alkylcarboxylic groups, $C_1$-$C_{20}$ linear or branched alkylcarboxamide groups, $C_1$-$C_{20}$ linear or branched alkylimino groups, $C_1$-$C_{20}$ linear or branched alkylsulphonic groups, $C_1$-$C_{20}$ linear or branched nitrile groups, $C_5$-$C_{40}$ aryl groups, and $C_6$-$C_{40}$ alkylaryl groups.

7. The compound according to claim 1, wherein $Ar^1$, $Ar^2$, $Ar^3$ and/or $Ar^4$, independently of each other, are selected from a group consisting of the following formulas (u), (v), (w), (x) and (y):

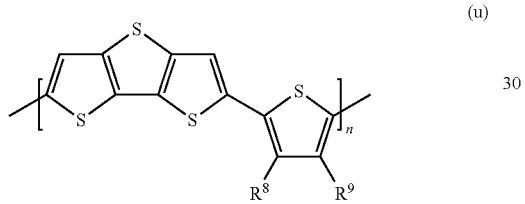
(u)

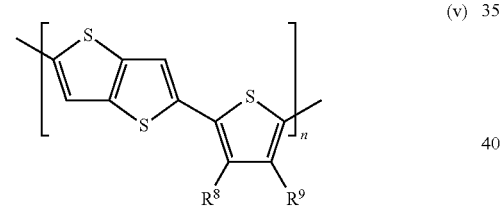
(v)

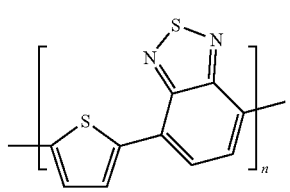
(w)

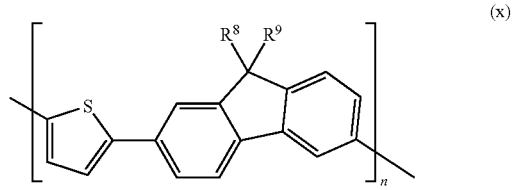
(x)

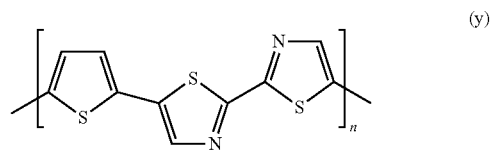
(y)

wherein n is comprised between 2 and 10 and $R^8$, $R^9$, independently of each other, are selected from a group consisting of hydrogen, halogens, $C_1$-$C_{20}$ linear or branched alkyl groups, $C_2$-$C_{20}$ linear or branched alkenyl groups, $C_2$-$C_{20}$ linear or branched alkynyl groups, $C_1$-$C_{20}$ linear or branched heteroalkyl groups, $C_2$-$C_{20}$ linear or branched heteroalkenyl groups, $C_2$-$C_{20}$ linear or branched heteroalkynyl groups, $C_3$-$C_{20}$ linear or branched cycloalkyl groups, $C_2$-$C_{20}$ linear or branched heterocycloalkyl groups, $C_2$-$C_{20}$ linear or branched alkylcarboxylic groups, $C_2$-$C_{20}$ linear or branched alkylcarboxamide groups, $C_2$-$C_{20}$ linear or branched alkylimino groups, $C_1$-$C_{20}$ linear or branched alkylsulphonic groups, $C_1$-$C_{20}$ linear or branched nitrile groups, $C_5$-$C_{40}$ aryl groups, and $C_6$-$C_{40}$ alkylaryl groups.

8. A compound having the following formula:

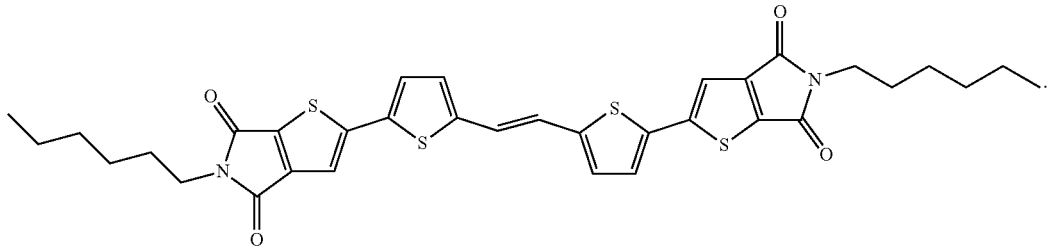 [SMILES: CCCCCCN1C(=O)c2cc(-c3ccc(/C=C/c4ccc(-c5cc6c(s5)C(=O)N(CCCCCC)C6=O)s4)s3)sc2C1=O]

9. An organic semiconductor material in an electronic device comprising the compound according to claim 1.

10. The organic semiconductor material in the electronic device according to claim 9, wherein the organic semiconductor material is an n-type organic semiconductor material.

11. An electronic device comprising a semiconductor layer in contact with a number of electrodes, wherein the semiconductor layer includes at least one compound according to claim 1.

12. A compound having formula (I):

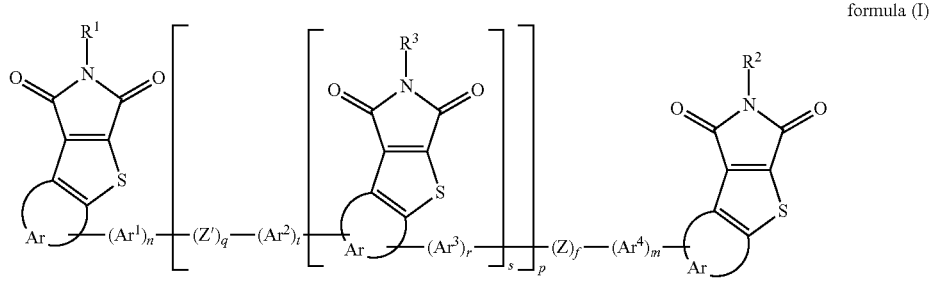

formula (I)

wherein:
R$^1$, R$^2$, R$^3$ independently of each other, are selected from a group consisting of C$_1$-C$_6$ linear alkyl groups, C$_6$ cycloalkyl groups, and C$_6$ unsubstituted and substituted monocyclic aryl groups;

Ar, Ar$^1$, Ar$^2$, Ar$^3$ and Ar$^4$, independently of each other, are moieties selected from a group consisting of a C$_6$ unsubstituted and substituted monocyclic aryl groups, C$_4$ unsubstituted and substituted monocyclic heteroaryl groups, and C$_6$ unsubstituted and substituted polycyclic heteroaryl groups or combinations thereof as dimers, trimers and tetramers;

Z and Z', independently of each other, are selected from a group consisting of bivalent radicals of formulas (III), (IV), (V), and (VI):

formula (III)
formula (IV)
formula (V)
formula (VI)

wherein G is selected from a group consisting of hydrogen, halogens, C$_1$-C$_{20}$ linear or branched alkyl groups, C$_2$-C$_{20}$ linear or branched alkenyl groups, C$_2$-C$_{20}$ linear or branched alkynyl groups, C$_1$-C$_{20}$ linear or branched heteroalkyl groups, C$_2$-C$_{20}$ linear or branched heteroalkenyl groups, C$_2$-C$_{20}$ linear or branched heteroalkynyl groups, C$_3$-C$_{20}$ linear or branched cycloalkyl groups, C$_3$-C$_{20}$ linear or branched heterocloalkyl groups, C$_2$-C$_{20}$ linear or branched alkylcarboxylic groups, C$_2$-C$_{20}$ linear or branched alkylcarboxamide groups, C$_2$-C$_{20}$ linear or branched alkylimino groups, C$_1$-C$_{20}$ linear or branched alkylsulphonic groups, C$_1$-C$_{20}$ linear or branched nitrile groups, C$_6$-C$_{50}$ unsubstituted and substituted monocyclic aryl groups, C$_{10}$-C$_{50}$ polycyclic aryl groups, C$_{10}$-C$_{50}$ substituted polycyclic aryl groups, C$_1$-C$_{50}$ unsubstituted and substituted monocyclic heteroaryl groups, C$_6$-C$_{50}$ polycyclic heteroaryl groups, and C$_6$-C$_{50}$ substituted polycyclic heteroaryl groups or combinations thereof;

s is 0 or 1;
n, m, r and t, independently of each other, are integers between 1 and 50;
q and f, independently of each other, are integers between 1 and 10; and
p is 0.

13. The compound according to claim 12, having formula (Ia):

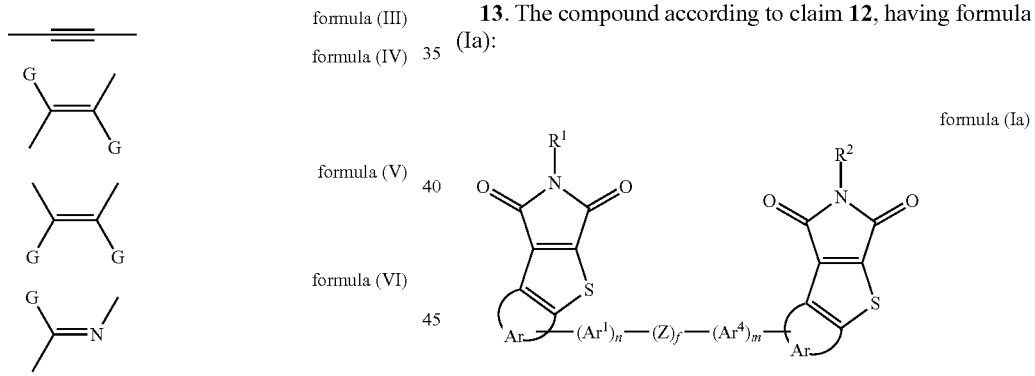

formula (Ia)

wherein R$^1$, R$^2$, Ar, Ar$^1$, Ar$^4$, Z, f, n, m are as specified in claim 12.

14. The compound according to claim 12, wherein q and f are each 1 or 2, and n, and m are between 2 and 10.

15. The compound according to claim 12, wherein Z' and/or Z are selected from a group consisting of ethynylene, cis-ethenylene and trans-ethenylene.

* * * * *